(12) United States Patent
Moore, Jr. et al.

(10) Patent No.: US 11,311,532 B2
(45) Date of Patent: *Apr. 26, 2022

(54) HIGH DOSAGE VALBENAZINE FORMULATION AND COMPOSITIONS, METHODS, AND KITS RELATED THERETO

(71) Applicant: Neurocrine Biosciences, Inc., San Diego, CA (US)

(72) Inventors: Richard Alexander Moore, Jr., San Diego, CA (US); Gregory A. McClelland, San Diego, CA (US); Christopher F. O'Brien, Vashon, WA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/074,383

(22) Filed: Oct. 19, 2020

(65) Prior Publication Data

US 2021/0030744 A1 Feb. 4, 2021

Related U.S. Application Data

(63) Continuation of application No. 16/646,866, filed as application No. PCT/US2018/051579 on Sep. 18, 2018, now abandoned.

(60) Provisional application No. 62/564,951, filed on Sep. 28, 2017, provisional application No. 62/561,629, filed on Sep. 21, 2017.

(51) Int. Cl.
| | |
|---|---|
| *A61K 31/4745* | (2006.01) |
| *A61K 9/00* | (2006.01) |
| *A61K 9/48* | (2006.01) |
| *A61K 47/02* | (2006.01) |
| *A61K 47/12* | (2006.01) |
| *A61K 47/26* | (2006.01) |
| *A61K 47/36* | (2006.01) |
| *A61K 47/38* | (2006.01) |

(52) U.S. Cl.
CPC ........ *A61K 31/4745* (2013.01); *A61K 9/0053* (2013.01); *A61K 9/48* (2013.01); *A61K 47/02* (2013.01); *A61K 47/12* (2013.01); *A61K 47/26* (2013.01); *A61K 47/36* (2013.01); *A61K 47/38* (2013.01)

(58) Field of Classification Search
CPC .... A61K 31/4745; A61K 9/0053; A61K 9/48; A61K 47/02; A61K 47/12; A61K 47/26; A61K 47/36; A61K 47/38
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,328,245 A | 5/1982 | Yu et al. |
| 4,409,239 A | 10/1983 | Yu |
| 4,410,545 A | 10/1983 | Yu et al. |
| 5,059,595 A | 10/1991 | Le Grazie |
| 5,073,543 A | 12/1991 | Marshall et al. |
| 5,120,548 A | 6/1992 | McClelland et al. |
| 5,354,556 A | 10/1994 | Sparks et al. |
| 5,591,767 A | 1/1997 | Mohr et al. |
| 5,612,059 A | 3/1997 | Cardinal et al. |
| 5,639,476 A | 6/1997 | Oshlack et al. |
| 5,639,480 A | 6/1997 | Bodmer et al. |
| 5,674,533 A | 10/1997 | Santus et al. |
| 5,698,220 A | 12/1997 | Cardinal et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gorewich |
| 5,798,119 A | 8/1998 | Herbig et al. |
| 5,840,674 A | 11/1998 | Yatvin et al. |
| 5,891,474 A | 4/1999 | Busetti et al. |
| 5,900,252 A | 5/1999 | Calanchi et al. |
| 5,922,356 A | 7/1999 | Koseki et al. |
| 5,972,366 A | 10/1999 | Heynes et al. |
| 5,972,891 A | 10/1999 | Kamei et al. |
| 5,980,945 A | 11/1999 | Ruiz |
| 5,985,307 A | 11/1999 | Hanson et al. |
| 5,993,855 A | 11/1999 | Yoshimoto et al. |

(Continued)

FOREIGN PATENT DOCUMENTS

| | | |
|---|---|---|
| CN | 1980942 | 6/2007 |
| CN | 106061506 | 10/2016 |

(Continued)

OTHER PUBLICATIONS

World Health Organization. Bulk Density and Tapped Density of Powders. Document QAS/11.450 Final, Mar. 2012, 6 pages. (Year: 2012).*
U.S. Appl. No. 16/481,034, filed Jul. 25, 2019, O'Brien et al.
U.S. Appl. No. 16/481,037, filed Jul. 25, 2019, O'Brien et al.
U.S. Appl. No. 16/509,552, filed Jul. 12, 2019, McGee et al.
U.S. Appl. No. 16/608,521, filed Oct. 25, 2019, O'Brien.
U.S. Appl. No. 16/646,866, filed Mar. 12, 2020, Moore, Jr et al.
U.S. Appl. No. 16/651,887, filed Mar. 27, 2020, O'Brien et al.
U.S. Appl. No. 16/662,346, filed Oct. 24, 2019, McGee et al.
U.S. Appl. No. 16/701,339, filed Dec. 3, 2019, O'Brien et al.

(Continued)

*Primary Examiner* — Robert A Wax
*Assistant Examiner* — Olga V. Tcherkasskaya
(74) *Attorney, Agent, or Firm* — Fish & Richardson P.C.

(57) ABSTRACT

Solid pharmaceutical compositions with high drug loading are provided. A formulation useful for the solid pharmaceutical composition includes valbenazine, or a pharmaceutically acceptable salt thereof, silicified microcrystalline cellulose, isomalt, hydroxypropyl methylcellulose, partially pregelatinized maize starch, and magnesium stearate.

32 Claims, 2 Drawing Sheets

(56) References Cited

U.S. PATENT DOCUMENTS

| | | |
|---|---|---|
| 6,004,534 A | 12/1999 | Langer et al. |
| 6,039,975 A | 3/2000 | Shah et al. |
| 6,045,830 A | 4/2000 | Igari et al. |
| 6,048,736 A | 4/2000 | Kosak |
| 6,060,082 A | 5/2000 | Chen et al. |
| 6,071,495 A | 6/2000 | Unger et al. |
| 6,087,324 A | 7/2000 | Igari et al. |
| 6,113,943 A | 9/2000 | Okada et al. |
| 6,120,751 A | 9/2000 | Unger |
| 6,131,570 A | 10/2000 | Schuster et al. |
| 6,139,865 A | 10/2000 | Friend et al. |
| 6,197,350 B1 | 3/2001 | Yamagata et al. |
| 6,248,363 B1 | 6/2001 | Patel et al. |
| 6,253,872 B1 | 7/2001 | Neumann |
| 6,264,970 B1 | 7/2001 | Hata et al. |
| 6,267,981 B1 | 7/2001 | Okamoto et al. |
| 6,271,359 B1 | 8/2001 | Norris et al. |
| 6,274,552 B1 | 8/2001 | Tamarkin et al. |
| 6,316,652 B1 | 11/2001 | Steliou |
| 6,350,458 B1 | 2/2002 | Modi |
| 6,376,461 B1 | 4/2002 | Igari et al. |
| 6,419,961 B1 | 7/2002 | Igari et al. |
| 6,589,548 B1 | 7/2003 | Oh et al. |
| 6,613,358 B2 | 9/2003 | Randolph et al. |
| 6,699,500 B2 | 3/2004 | Okada et al. |
| 8,039,627 B2 | 10/2011 | Gano et al. |
| 8,357,697 B2 | 1/2013 | Gano et al. |
| 8,524,733 B2 | 9/2013 | Gant et al. |
| 9,714,246 B2 | 7/2017 | Ashweek et al. |
| 9,782,398 B2 | 10/2017 | Hoare et al. |
| 10,065,952 B2 | 9/2018 | McGee et al. |
| 10,160,757 B2 | 12/2018 | McGee et al. |
| 10,689,380 B1 | 6/2020 | Lopez |
| 10,857,137 B2 | 12/2020 | O'Brien et al. |
| 10,874,648 B2 | 12/2020 | O'Brien et al. |
| 10,906,902 B2 | 2/2021 | McGee et al. |
| 10,906,903 B2 | 2/2021 | McGee et al. |
| 10,912,771 B1 | 2/2021 | O'Brien et al. |
| 10,919,892 B2 | 2/2021 | McGee et al. |
| 10,952,997 B2 | 3/2021 | O'Brien et al. |
| 10,993,941 B2 | 5/2021 | O'Brien et al. |
| 11,026,931 B2 | 6/2021 | Liang et al. |
| 11,026,939 B2 | 6/2021 | Moore, Jr. et al. |
| 11,040,029 B2 | 6/2021 | O'Brien et al. |
| 2006/0051345 A1 | 3/2006 | Frohna |
| 2006/0241082 A1 | 10/2006 | Fleckenstein et al. |
| 2008/0108645 A1 | 5/2008 | Tridgett et al. |
| 2008/0167337 A1 | 7/2008 | Gano |
| 2009/0209755 A1 | 8/2009 | Suzuki et al. |
| 2010/0076087 A1 | 3/2010 | Gant et al. |
| 2010/0204259 A1* | 8/2010 | Tygesen ............... A61K 9/2866 514/282 |
| 2010/0317746 A1* | 12/2010 | Kowalczyk ........... A61K 9/145 514/778 |
| 2011/0053866 A1 | 3/2011 | Duffield et al. |
| 2012/0003330 A1 | 1/2012 | Gant et al. |
| 2012/0077839 A1 | 3/2012 | Gano et al. |
| 2014/0187505 A1 | 7/2014 | Pollard |
| 2014/0341994 A1 | 11/2014 | Sommer et al. |
| 2015/0004231 A1 | 1/2015 | Sommer et al. |
| 2015/0025086 A1 | 1/2015 | Dressman et al. |
| 2016/0030414 A1 | 2/2016 | Gant et al. |
| 2016/0339011 A1 | 11/2016 | Hoare et al. |
| 2016/0346200 A1 | 12/2016 | Sommer et al. |
| 2016/0346270 A1 | 12/2016 | Stamler |
| 2017/0071932 A1 | 3/2017 | O'Brien |
| 2017/0145008 A1 | 5/2017 | McGee et al. |
| 2017/0183346 A1 | 6/2017 | McGee et al. |
| 2018/0085364 A1 | 3/2018 | Hoare |
| 2018/0280374 A1 | 10/2018 | Duffield et al. |
| 2018/0333409 A1 | 11/2018 | Srinivasan et al. |
| 2019/0015396 A1 | 1/2019 | O'Brien et al. |
| 2019/0262328 A1 | 8/2019 | Srinivasan et al. |
| 2019/0381016 A1 | 12/2019 | O'Brien et al. |
| 2019/0381029 A1 | 12/2019 | Hoare et al. |
| 2020/0078352 A1 | 3/2020 | O'Brien et al. |
| 2020/0093808 A1 | 3/2020 | O'Brien et al. |
| 2020/0101063 A1 | 4/2020 | O'Brien et al. |
| 2020/0179352 A1 | 6/2020 | O'Brien |
| 2020/0181140 A1 | 6/2020 | McGee et al. |
| 2020/0206215 A1 | 7/2020 | Hoare et al. |
| 2020/0230127 A1 | 7/2020 | O'Brien et al. |
| 2020/0268724 A1 | 8/2020 | O'Brien et al. |
| 2020/0268725 A1 | 8/2020 | O'Brien et al. |
| 2020/0268743 A1 | 8/2020 | O'Brien et al. |
| 2020/0268744 A1 | 8/2020 | O'Brien et al. |
| 2020/0268745 A1 | 8/2020 | O'Brien et al. |
| 2020/0276184 A1 | 9/2020 | Moore, Jr. et al. |
| 2020/0338066 A1 | 10/2020 | O'Brien et al. |
| 2020/0339574 A1 | 10/2020 | McGee et al. |
| 2020/0339575 A1 | 10/2020 | McGee et al. |
| 2020/0339576 A1 | 10/2020 | McGee et al. |
| 2020/0347054 A1 | 11/2020 | McGee et al. |
| 2020/0347055 A1 | 11/2020 | McGee et al. |
| 2020/0347056 A1 | 11/2020 | McGee et al. |
| 2020/0347057 A1 | 11/2020 | McGee et al. |
| 2020/0360354 A1 | 11/2020 | Liang et al. |
| 2020/0397779 A1 | 12/2020 | Liang et al. |
| 2021/0030742 A1 | 2/2021 | O'Brien et al. |
| 2021/0030743 A1 | 2/2021 | Moore, Jr. et al. |
| 2021/0038593 A1 | 2/2021 | O'Brien |
| 2021/0046060 A1 | 2/2021 | O'Brien et al. |
| 2021/0052558 A1 | 2/2021 | Lowen et al. |
| 2021/0113553 A1 | 4/2021 | O'Brien et al. |
| 2021/0169862 A1 | 6/2021 | O'Brien et al. |
| 2021/0196702 A1 | 7/2021 | O'Brien et al. |

FOREIGN PATENT DOCUMENTS

| | | |
|---|---|---|
| EA | 018378 | 7/2013 |
| EP | 1716145 | 11/2006 |
| GB | 2463452 | 3/2010 |
| JP | S 52-083918 | 7/1977 |
| JP | 57-077697 | 5/1982 |
| JP | 57-209225 | 12/1982 |
| JP | S 60-028987 | 2/1985 |
| JP | 2007-522193 | 8/2007 |
| JP | 2008-518911 | 6/2008 |
| JP | 2009-504622 | 2/2009 |
| JP | 2012-522838 | 9/2012 |
| JP | 2016-506957 | 3/2016 |
| JP | 2017-514850 | 6/2017 |
| WO | WO 1991/019498 | 12/1991 |
| WO | WO 1998/011897 | 3/1998 |
| WO | WO 2000/024399 | 5/2000 |
| WO | WO 2002/017918 | 3/2002 |
| WO | WO 2004/085435 | 10/2004 |
| WO | WO 2005/077946 | 8/2005 |
| WO | WO 2006/053067 | 5/2006 |
| WO | WO 2007/017654 | 2/2007 |
| WO | WO 2008/058261 | 5/2008 |
| WO | WO 2009/056885 | 5/2009 |
| WO | WO 2010/018408 | 2/2010 |
| WO | WO 2010/026435 | 3/2010 |
| WO | WO 2010/026436 | 3/2010 |
| WO | WO 2010/044961 | 4/2010 |
| WO | WO 2010/044981 | 4/2010 |
| WO | WO 2011/019956 | 2/2011 |
| WO | WO 2011/153157 | 12/2011 |
| WO | WO 2012/153341 | 11/2012 |
| WO | WO 2014/047167 | 3/2014 |
| WO | WO 2014/120654 | 8/2014 |
| WO | WO 2015/077521 | 5/2015 |
| WO | WO 2015/112707 | 7/2015 |
| WO | WO 2015/120110 | 8/2015 |
| WO | WO 2015/120317 | 8/2015 |
| WO | WO 2015/171802 | 11/2015 |
| WO | WO 2016/127133 | 8/2016 |
| WO | WO 2016/144901 | 9/2016 |
| WO | WO 2016/210180 | 12/2016 |
| WO | WO 2017/075340 | 5/2017 |
| WO | WO 2017/112857 | 6/2017 |
| WO | WO 2018/102673 | 6/2018 |
| WO | WO 2018/140092 | 8/2018 |

(56) References Cited

FOREIGN PATENT DOCUMENTS

| WO | WO 2018/140093 | 8/2018 |
|----|----------------|--------|
| WO | WO 2018/140094 | 8/2018 |
| WO | WO 2018/140095 | 8/2018 |
| WO | WO 2018/140096 | 8/2018 |
| WO | WO 2018/178233 | 10/2018 |
| WO | WO 2018/178243 | 10/2018 |
| WO | WO 2018/195121 | 10/2018 |
| WO | WO 2018/200605 | 11/2018 |
| WO | WO 2019/060322 | 3/2019 |
| WO | WO 2019/074492 | 4/2019 |
| WO | WO 2019/104141 | 5/2019 |
| WO | WO 2019/241555 | 12/2019 |
| WO | WO 2020/037022 | 2/2020 |

OTHER PUBLICATIONS

U.S. Appl. No. 16/754,658, filed Apr. 8, 2020, O'Brien et al.
U.S. Appl. No. 16/817,723, filed Mar. 13, 2020, Hoare et al.
U.S. Appl. No. 16/845,134, filed Apr. 10, 2020, O'Brien et al.
U.S. Appl. No. 16/870,423, filed May 8, 2020, O'Brien et al.
U.S. Appl. No. 16/870,572, filed May 8, 2020, O'Brien et al.
U.S. Appl. No. 16/870,706, filed May 8, 2020, O'Brien et al.
U.S. Appl. No. 16/870,823, filed May 8, 2020, O'Brien et al.
U.S. Appl. No. 16/871,528, filed May 11, 2020, O'Brien et al.
U.S. Appl. No. 16/929,694, filed Jul. 15, 2020, McGee et al.
U.S. Appl. No. 16/929,696, filed Jul. 15, 2020, McGee et al.
U.S. Appl. No. 16/929,714, filed Jul. 15, 2020, McGee et al.
U.S. Appl. No. 16/929,716, filed Jul. 15, 2020, McGee et al.
U.S. Appl. No. 16/983,334, filed Aug. 3, 2020, Liang et al.
U.S. Appl. No. 16/989,206, filed Aug. 10, 2020, Loewen et al.
U.S. Appl. No. 17/005,425, filed Aug. 28, 2020, O'Brien.
U.S. Appl. No. 17/021,362, filed Sep. 15, 2020, O'Brien et al.
U.S. Appl. No. 17/074,278, filed Oct. 19, 2020, Moore, Jr et al.
"Cytochrome P450 Oxidoreductase (POR) Deficiency," GeneDx, 2016, 5 pages.
"Neurocrine Valbenazine," Science IP Order 3198386, Oct. 2, 2019, 92 pages.
[No Author Listed], "Cytochrome P450 3A4 and 3A5 known drug interaction chart," 2014, 2 pages.
[No Author Listed], "Drug interactions with CYP3 A inducers and inhibitors for Torisel (temsirolimus) injection," Wyeth Pharmaceuticals, 2008, 12 pages.
[No Author Listed], "Physician guidelines: drugs metabolized by cytochrome P450's," Genelex Corporation, 2005, 4 pages.
[No Author Listed,]"Ingrezza Prescription Information," Neurocrine Biosciences, Apr. 2017, 16 pages.
Alexander et al., "Increased aggression in males in transgenic Tg2576 mouse model of Alzheimer's disease," Behav Brain Res., 216(1):77-83.
Anonymous, "11th Annual Meeting Schedule," ASENT, Mar. 5-7, 2009, 3 pages.
Anonymous, "12th Annual Meeting Program," ASENT, Bethesda, Maryland, Mar. 4-6, 2010, 1 page.
Anonymous, "Neurocrine Announces Phase IIb Results of VMAT2 Inhibitor NB1-98854 for Treatment of Tardive Dyskinesia," Neurocrine Biosciences: Investors: PressRelease, Sep. 9, 2013, [retrieved on Dec. 13, 2018] retrieved from URL<http://phoenix.corporate-ir.net/phoenix.zhtml?c=68817&p=irol-newsArticle_Print&ID=1853185>, 7 pages.
Australian Office Action in AU Appln. No. 2015256012, dated May 26, 2020, 5 pages.
Ballard et al., "Management of Agitation and Aggression Associated with Alzheimer's disease: controversies and possible solutions," Curr Opin in Psych., Nov. 2009, 22(6):532-540.
Ballard et al., "Neuroleptic drugs in dementia: benefits and harm," Nat Rev Neurosci., Jun. 2006, 7:492-500.
Ballard et al., "Quetiapine and rivastigmine and cognitive decline in Alzheimer's disease: randomised double blind placebo controlled trial," BMJ, Apr. 16, 2005, 330:874-877.

Bastin et al., "Salt Selection and Optimisation Procedures for Pharmaceutical New Chemical Entities," Organic Process Res. Dev., 2000, 4(5):427-435.
Bauer, "Pharmaceutical Solids—The Amorphous Phase," J Validation Tech., 2009, 15(3):63-68.
Berge et al., "Pharmaceutical Salts," J Pharm Sci., Jan. 1977, 66(1):1-19.
Bhidayasiri and Boonyawairoj, "Spectrum of tardive syndromes: clinical recognition and management.," Postgrad Med J, Feb. 2011, 87(1024): 132-141.
Boldt et al., "Synthesis of (+)- and (−)-Tetrabenazine from the Resolution of [alpha]-Dihydrotetrabenazine," Synthetic Communications, 2009, 39(20):3574-3585.
Brunner et al., "Comprehensive Analysis of the 16p11.2 Deletion and Null Cntnap2 Mouse Models of Autism Spectrum Disorder," PLoS One, Aug. 14, 2015, 10(8):e0134572.
Brusa et al., "Tetrabenazine improves levodopa-induced peak-dose dyskinesias in patients with Parkinson's disease," Funct. Neural., 2013, 28(2):101-5.
Bystritsky, "Treatment-resistant anxiety disorders," Mol. Psychiatry, Sep. 2006, 11(9):805-814.
Caira et al., "Crystalline Polymorphism of Organic Compounds," Topics in Current Chemistry, 1998, 198(36):163-208.
Caroff et al., "Treatment of tardive dyskinesia with tetrabenazine or valbenazine: a systematic review," J. Com. Eff. Research, 2017, 7(2):135-148.
Center for Drug Evaluation and Research Application No. 2092410 ("Publication No. 2092410"), Clinical Pharmacology and Biopharmaceuticals Review, Submission Date Aug. 11, 2016.
Chinese Office Action in Chinese Application No. 201580023821. X, dated Jun. 20, 2018, 10 pages.
Citrome, "Valbenazine for tardive dyskinesia: A systematic review of the efficacy and safety profile for this newly approved novel medication—What is the number needed to treat, number needed to harm and likelihood to be helped or harmed?," Int J Clin Pract., 2017, e12964.
Cohen-Mansfield et al., "A description of agitation in a nursing home," J Gerontol., May 1989, 44(3):M77-M84.
Correll and Schenk, "Tardive dyskinesia and new antipsychotics," Curr Opin Psychiatry, Mar. 2008, 21(2):151-156.
Corvin, "Two patients walk into a clinic . . . a genomics perspective on the future of schizophreniam," BMC Biol., 2011, 8 pages.
Cummings et al., "Deuterium tetrabenazine for tardive dyskinesia," Clinical Schizophrenia & Related Psychoses, 2018, 214-220.
Cummings et al., "The Neuropsychiatric Inventory: comprehensive assessment of psychopathology in dementia," Neurology, 1994, 44:2308-2314.
Davis et al., "Center For Dmg Evaluation And Research," Medical Reviews(s), 2017, Accessed on Sep. 30, 2020, retrieved from URL<https://www.accessdata.fda.gov/drugsatfda_docs/nda/2017/209241Orig1s000MedR.pdf>, 297 pages.
Derangula et al, "Liquid chromatography-tandem mass spectrometric assay for the determination of tetrabenazine and its active metabolites in human plasma: a pharmacokinetic study," Biomedical Chromatography, Jun. 2013, 27(6):792-801.
Drug Development and Drug Interactions: Table of Substrates, Inhibitor and Inducers at https://www.fda.gov/drugs/developmentapprovalprocess/developmentesources/druginteractionslabeling/ucm093664.htm, U.S. Food and Drug Administration, 2017, 18 pages.
Erickson et al., "Reserpine- and tetrabenazine-sensitive transport of (3)H-histamine by the neuronal isoform of the vesicular monoamine transporter," Journal of Molecular Neuroscience, 1995, 6(4):277-287.
Eurasian Office Action in Eurasian Application No. 201890108, dated Oct. 30, 2018, 5 pages.
European Office Action in European Application No. 15734438.5, dated Jul. 17, 2018, 4 pages.
Extended European Search Report in European Appln. No. 16734150. 2, dated Apr. 11, 2019, 7 pages.
Fahr, "Kapseln," Pharmazeutische Technologie, Jan. 2000, p. 237 (with machine English translation).

(56) References Cited

OTHER PUBLICATIONS

Fda.gov [online], U.S. Food & Drug Administration Drug Approvals and Databases, "Ingrezza (valbenazine) Capsules," dated Jun. 1, 2017, retrieved on Sep. 30, 2020, retrieved from URL<https://www.accessdata.fda.gov/drugsatfda_docs/nda/2017/209241Orig1s000TOC.cfm>, 2 pages.
Fields et al., "Pill Properties that Cause Dysphagia and Treatment Failure," Current Therapeutic Research, Aug. 2015, 77:79-82.
Foster et al., "Deuterium isotope effects in the metabolism of drugs and xenobiotics: implications for drug design," Adv Drug Res., 1985, 14:1-36.
Gantois et al., "Restoring the phenotype of fragile X syndrome: insight from the mouse model," Curr Mol Med., Sep. 2001, 1(4):447-455.
Gately et al., "Deuterioglucose: alteration of biodistribution by an isotope effect," J Nucl Ned., 1986, 27(3):388-394.
Gordon et al., "The metabolism of the abortifacient terpene, (R)-(+)-pulegone, to a proximate toxin, menthofuran," Drug Metab Disp., 1987, 15(5):589-594.
Gottlieb et al., "NMR Chemical Shifts of Common Laboratory Solvents as Trace Impurities," J. Org. Chem. 1997, 62 (21): 7512-7515.
Grigoriadis et al., "Pharmacologic characterization of valbenazine (NBI-98854) and its metabolites," Journal of Pharmacology and Experimental Therapeutics, 2017, 361(3):454-461.
Guilloteau et al., "PET and SPECT exploration of central monoaminergic transporters for the development of new drugs and treatments in brain disorders," Current Pharmaceutical Design, Jan. 1, 2005, 11(25):3237-3245.
Gulieva et al., "Neuropharmacology analysis of the effect of olanzapine and clozapine on behavior characteristics and neuromodulator content in rat brain structure," Psychopharmacology and biological necrology, 2004, 585-589.
Guridi et al., "Clinical Features, Pathophysiology, and Treatment of Levodopa-Induced Dyskinesias in Parkinson's Disease," Parkinson's Disease, 2012, 1-15.
Harriot et al., "Identification of the First Selective Small Molecule BB2 Antagonists," Poster, Presented at the 249th ACS National Meeting & Exposition, Denver CO, Mar. 22-26, 2015, 1 page.
Harris Interactive Inc. for Schwarz Pharma, 2003, Pill-Swallowing Problems in America: A National Surey of Adults. 1-39.
Hauser et al., "KINECT 3: A phase 3 randomized, double-blind, placebo-controlled trial of valbenazine for tardive dyskinesia," American Journal of Psychiatry, 2016, 174(5):476-484.
Healy et al., "Clozapine-reserpine combination for refractory psychosis," Schizophrenia Research, Jan. 1, 1997, 25:259-260.
Herrmann et al., "A Placebo-Controlled Trial of Valproate for Agitation and Aggression in Alzheimer's Disease," Dement Geriatr Cogn Disord., Jan. 2007, 23:116-119.
Hoare et al., "Conformational states of the corticotropin releasing factor 1 (CRF1) receptor: detection, and pharmacological evaluation by peptide ligands," Peptides, Dec. 2003, 24(12):1881-1897.
Horev et al., "Dosage-dependent phenotypes in models of 16p11.2 lesions found in autism," Proc Natl Acad Sci USA., 2011, 108(41):17076-17081.
Howard et al., "Guidelines for the management of agitation in dementia," Int. J. Geriatr. Psychitry, Jul. 2001, 16(7):714-717.
Hu, "New Fluorescent Substrate Enables Quantitative and High-throughput Examination of Vesicular Monoamine Transporter 2 (VMAT2)," ACS Chem Biol. Sep. 20, 2013,:8(9):1947-1954.
Ingrezza, Highlights of Prescribing Information, Neurocrine Biosciences, Inc., revised Oct. 2017, 15 pages.
Ingrezza, Patient Information, Neurocrine Biosciences, Inc., revised Oct. 2017, 1 page.
International Preliminary Report on Patentability in Appln. No. PCT/US2017/055907, dated Apr. 14, 2020, 18 pages.
International Preliminary Report on Patentability in Appln. No. PCT/US2017/055947, dated Apr. 23, 2020, 10 pages.
International Preliminary Report on Patentability in Appln. No. PCT/US2018/029255, dated Oct. 29, 2019, 7 pages.
International Preliminary Report on Patentability in International Application No. PCT/US2016/039098, dated Dec. 26, 2017, 8 pages.
International Preliminary Report on Patentability in International Application No. PCT/US2017/055877, dated Jul. 30, 2019, 11 pages.
International Preliminary Report on Patentability in International Application No. PCT/US2017/055931, dated Jul. 30, 2019, 16 pages.
International Preliminary Report on Patentability in International Application No. PCT/US2017/055965, dated Jul. 30, 2019, 8 pages.
International Preliminary Report on Patentability in International Application No. PCT/US2017/055980, dated Jul. 30, 2019, 7 pages.
International Preliminary Report on Patentability in International Appln. No. PCT/US2017/064196, dated Jun. 4, 2019, 6 pages.
International Report on Patentability in International Application No. PCT/US2015/029519, dated Nov. 8, 2016, 8 pages.
International Search Report and Written Opinion in Appln. No. PCT/US2017/055877, dated Dec. 26, 2019, 11 pages.
International Search Report and Written Opinion in Appln. No. PCT/US2017/055907, dated Dec. 5, 2017, 21 pages.
International Search Report and Written Opinion in Appln. No. PCT/US2017/055931, dated Dec. 11, 2017, 17 pages.
International Search Report and Written Opinion in Appln. No. PCT/US2017/55965, dated Dec. 5, 2017, 9 pages.
International Search Report and Written Opinion in Appln. No. PCT/US2018/029255, dated Jun. 26, 2018, 9 pages.
International Search Report and Written Opinion in Appln. No. PCT/US2017/55980, dated Dec. 1, 2017, 9 pages.
International Search Report and Written Opinion in International Application No. PCT/US2015/029519, dated Jun. 21, 2015, 11 pages.
International Search Report and Written Opinion in International Application No. PCT/US2016/039098, dated Nov. 22, 2016, 15 pages.
International Search Report and Written Opinion in International Appln. No. PCT/US2017/064196, dated Feb. 21, 2018, 10 pages.
International Search Report and Written Opinion in International Appln. No. PCT/US2019/46462, dated Nov. 7, 2019, 14 pages.
International Search Report in Appln. No. PCT/US2017/055947, dated Dec. 5, 2017, 8 pages.
Jacq et al., "Development and validation of an automated static headspace gas chromatography-mass spectrometry (SHS-GC-MS) method for monitoring the formation of ethyl methane sulfonate from ethanol and methane sulfonic acid," J Pharm. Biomed Anal., 2008, 48(5):1339-1344.
Jankovic and Beach, "Long-term effects of tetrabenazine in hyperkinetic movement disorders," Neurology, Feb. 1, 1997, 48(2):359-362.
Jankovic et al., "Lesch-Nyhan Syndrome. A Study of Motor Behaviour and Cerebrospinal Fluid Neurotransmitters," Ann Neuro., May 1988, 23(5):466-469.
Jankovic., "Dopamine depleters in the treatment of hyperkinetic movement disorders," Expert Opinion on Pharmacotherapy, 17.18, 2016, 2461-2470.
Japanese Office Action in Japanese Application No. 2016-566238, dated Feb. 12, 2019, 13 pages.
Jiang, "Application of Deuteration in Drag Research," Qilu Pharmacautical Affairs, 29(11):682-684.
Jinnah et al., "Amphetamine-induced behavioral phenotype in a hypoxanthine-guanine phosphoribosyltransferase-deficient mouse model of Lesch-Nyhan syndrome," Behav Neurosci., Dec. 1991, 105(4):1004-1012.
Josiassen et al., "Long-term safety and tolerability of valbenazine (NBI-98854) in subjects with tardive dyskinesia and a diagnosis of Schizophrenia or mood disorder," Psychopharmacology Bulletin, 2017, 47(3):61-68.
Jul et al., "Hyperactivity with Agitative-Like Behavior in a Mouse Tauopathy Model," J Alzheimer's Dis., 2015, 49(3):783-795.
Katz et al., "Preclinical research in Rett syndrome: setting the foundation for translational success," Disease Models & Mechanisms, 2012, 5:733-745.
Kay et al., "The Positive and Negative Syndrome Scale (PANSS) for Schizophrenia," Schizophrenia Bulletin, 1987, 13:262-276.

(56) References Cited

OTHER PUBLICATIONS

Kazdoba et al., "Modeling fragile X syndrome in the Fmr1 knockout mouse," Intractable Rare Dis Res., Nov. 2014, 3(4):118-133.
Kenney et al., "Long-Term Tolerability of Tetrabenazine in the Treatment of Hyperkinetic Movement Disorders," Movement Disorders, 2007, 22(2):193-197.
Kenney et al., "Tetrabenazine in the treatment of hyperkinetic movement disorders," Expert Review Neurotherapeutics, 2006, 6(1):7-17.
Khalsa et al., "Treatment-resistant OCD: Options beyond first-line medications," Curr. Psychiatry, 2011, 10(11):45-52.
Kilbourn et al., "Absolute configuration of (+)-alpha-dihydrotetrabenazine, an active metabolite of tetrabenazine," Chiralty, 1997, 9:(1)59-62.
Kilbourn et al., "Binding of alpha-dihydrotetrabenazine to the vesicular monoamine transporter is stereospecific," Eur J Pharmacol May 24, 1995, 278(3):249-252.
Kilbourn et al., "In vivo binding of (+)-alpha-[3H]dihydrotetrabenazine to the vesicular monoamine transporter of rat brain: bolus vs. equilibrium studies," European Journal of Pharmacology, 1997, 331(2-3):161-168.
Kilbourn et al., "In vivo measures of dopaminergic radioligands in the rat brain: equilibrium infusion studies," Synapse, Mar. 1, 2002, 43(3):188-194.
Kim, "Valbenazine: First Global Approval," Drugs, 2017, 77:1123-1129.
Kimiagar er al., "Rapid improvement of tardive dyskinesia with tetrabenazine, clonazepam and clozapine combined: a naturalistic long-term follow-up study," J Neurol., Nov. 9, 2011, 259(4):660-664.
Koch et al., "Successful Therapy of Tardive Dyskinesia in a 71-year-old Woman with a combination of Tetrabenazine, Olanzapine and Tiapride," IJCP, Mar. 1, 2003, 57(2):147-149.
Kuehn et al., "A potential animal model for Lesch-Nyhan syndrome through introduction of HPRT mutations into mice," Nature, Mar. 1987, 326(6110):295-298.
Kurlan, "Treatment of Tourette Syndrome," Neurotherapeutics, 2014, 11:161-165.
Kushner et al., "Pharmacological uses and perspectives of heavy water and deuterated compounds," Can J Physiol Pharmacol., 1999, 77(2):79-88.
Lee et al., "In vitro and in vivo studies of benzisoquinoline ligands for the brain synaptic vesicle monoamine transporter," J. Med Chem., Jan. 5, 1996, 39(1):191-196.
Lijinsky et al., "Dose-response studies in carcinogenesis by nitroso-N-methyl-N-(2-phenyl)ethylamine in rats and the effects of deuterium substitution," Food Cosmet. Toxicol., Aug. 1982, 20(4):393-399.
Lijinsky et al., "Dose-response studies with nitrosoheptamethyleneimine and its alpha-deuterium-labeled derivative in F344 rats," J Natl Cancer Inst., Nov. 1982, 69(5):1127-1133.
Loewen et al., "Evaluation of the potential for concomitant medications to affect valbenazine pharmacokinetics," Poster, Presented at the American Society of Clinical Psychopharmacology, May 29-Jun. 2, 2017: Miami, FL, 1 page.
Loewen et al., "Evaluation of the potential for valbenzaine to elicit drug interactions," Poster, Presented at The American Society of Clinical Psychopharmacology, May 29-Jun. 2, 2017: Miami, FL, 1 page.
Lombroso et al., "Tourette Syndrome and Obsessive-Compulsive Disorder," Brain Dev., 2008, 30(4): 231-237.
Loriot et al., "Drug insight: gastrointestinal and hepatic adverse effects of molecular-targeted agents in cancer therapy," Nature Clinical Practice Oncology, 2008, 5(5):268-278.
Luo et al., "Single dose and repeat once-daily dose safety, tolerability, and pharmacokinetics of valbenazine in healthy male subjects," Poster, Presented at The American Psychiatric Association Annual Meeting, May 20-24, 2017, San Diego, CA, 1 page.
Madan, Invited Speaker, "NBI-98854: Human pharmacokinetics of NB1-98854 a selective inhibitory of VMAT2 with an attractive PK and safety profile for hyperkinetic movement disorders," Pipeline Projects Session, 12th annual meeting of American Society for Experimental NeuroTherapeutics, Bethesda, MD, 2010, 5 slides.
Madan, Invited Speaker, "NBI-98854: Selective inhibitor of VMAT2 with an attractive PK and safety profile for hyperkinetic movement disorders," Pipeline Projects Session, 11th annual meeting of American Society for Experimental NeuroTherapeutics, Arlington, VA, 2009, 9 slides.
Mangold et al., "Effects of deuterium labeling on azido amino acid mutagenicity in *Salmonella typhimurium*," Mutation Res., 1994, 308(1):33-42.
Marder et al., "Kinect 3: a randomized, double-blind, placebo-controlled phase 3 trial of valbenazine (NBI-98854) for Tardive Dyskinesia," American Academy of Neurology, 2016, 9 pages.
Margolese et al., "Tardive dyskinesia in the era of typical and atypical antipsychotics. Part 1: pathophysiology and mechanisms of induction," Can J Psychiatry, Aug. 2005, 50(9):541-47.
Material Safety Data Sheet. Product Name Valbenazine tosylate. Published May 1, 2014 (see Revision date). Retrieved from internet May 23, 2020. URL: https://www.selleckchem.com/msds/MSDS_S9500.pdf.
McBride et al., "Using *Drosophila* as a tool to identify Pharmacological Therapies for Fragile X Syndrome," Drug Discov Today Technol., Sep. 24, 2012, 10(1):e129-e136.
Mehvar et al., "Pharmacokinetics of tetrabenazine and its major metabolite in man and rat. Bioavailability and dose dependency studies," Drug Metabolism and Distribution, 1987, 15(2):250-255.
Mentalhealthamerica.net [online], "Depression," [retrieved on Dec. 17, 2018], retrieved from URL<http://www.mentalhealthamerica.net/conditions/depression>, 3 pages.
Mineur et al., "Social behavior deficits in the Fmr1 mutant mouse," Behav Breain Res., Mar. 15, 2006, 168(1):172-175.
Muller et al., "Valbenazine for the treatment of tardive dyskinesia," Expert Review of Neurotherapeutics, 2017, 17(2):1135-1144.
Muller, "Valbenazine granted breakthrough drug status for treating tardive dyskinesia," Expert Opin Investig Drugs, 2015, 24(6):737-42.
Near, "[3H]Dihydrotetrabenazine binding to bovine striatal synaptic vesicles," Mol. Pharmacol., Sep. 1986, 30:252-257.
Nikoloff et al., "Association between CYP2D6 genotype and tardive dyskinesia in Korean schizoprenics," The Pharmacogenomics J, 2002, 2:400-407.
Ninds.nih.gov [online], Available on or before Jan. 24, 2013, via Internet Archive: Wayback Machine URL <https://web.archive.org/web/20130124115120/www.ninds.nih.gov/disorders/rett/detail_rett.htm>, retrieved on Dec. 17, 2018], retrieved from URL<www.ninds.nih.gov/disorders/rett/detail_rett.htm>, 6 pages.
Nunes et al., "Effort-related motivational effects of the VMAT-2 inhibitor tetrabenazine: implications for animal models of the motivational symptoms of depression," J. Neurosci., 2013, 33(49):19120-30.
Nyhan et al., "Lesch-Nyhan Syndrome," Posted Sep. 25, 2000[last update May 15, 2014], 21 pages.
O'Brien et al., "NBI-98854, a selective monoamine transport inhibitor for the treatment of tardive dyskinesia: a randomized, double-blind, placebo-controlled study," Movement Disorders, 2015, 30(12):1681-1687.
Ondo et al, "Tetrabenazine treatment for tardive dyskinesia: assessment by randomized videotape protocol," Am J Psychiatry, Aug. 1999, 156(8):1279-1281.
Owesson-White et al., "Sources contributing to the average extracellular concentration of dopamine in the nucleus accumbens," J Neurochem., 2012, 121:252-62.
Pallanti and Quercioli, "Treatment-refractory obsessive-compulsive disorder: methodological issues, operational definitions and therapeutic lines," Neuropsychopharmacol. Biol Psychiatry, May 2006, 30(3):400-412.
PCT International Preliminary Report on Patentability in International Appln. No. PCT/US2018/051579, dated Apr. 2, 2020, 25 pages.
PCT International Search Report and Written Opinion in International Appln. No. PCT/US2018/051579, dated Mar. 18, 2019, 36 pages.

(56) References Cited

OTHER PUBLICATIONS

PCT International Search Report and Written Opinion in International Appln. No. PCT/US2020/032188, dated Oct. 2, 2020, 23 pages.
Piccinni et al., "Effectiveness of a Clozapine-Aripiprazole Combination in Tourette Syndrome and Bipolar Spectrum Disorder," J Neuropsychiatry Clin Neurosci., Jan. 1, 2013, 25:1.
Pincus, "Management of digoxin toxicity," Aust. Prescr., 2016, 39(1):18-21.
Pittenger et al., "Pharmacological treatment of obsessive-compulsive disorder," Psychiatr. Clin. North Am., 2014, 37(3):375-391.
Poliak et al., "Juxtaparanodal clustering of Shaker-like K+ channels in myelinated axons depends on Caspr2 and TAG-1," J Cell Biol., Sep. 15, 2003, 162(6):1149-1160.
Porta et al., "Tourette's syndrome and role of tetrabenazine," Clin Drug Invest., 2008, 28(7):443-459.
Portman et al., "Behavioral abnormalities and circuit defects in the basal ganglia of a mouse model of 16p11.2 deletion syndrome," Cell Rep., May 22, 2014, 7(4):1077-1092.
Prescott, "Powder handling," Pharmaceutical Process Scale-Up, Jan. 2011, 195-209.
Preswick Pharmaceuticals et al., "Xenazine (tetrabenazine) tablets," 2008, retrieved from URL: https://accessdata.fda.gov/drugsatfda_docs/label/2011/021894s0051b1.pdj, retrieved on Jul. 28, 2020, 27 pages.
Provenzano et al., "Mutant mouse models of autism spectrum disorders," Dis. Markers, 2012, 33(5):225-239.
Rao et al, "Review article: metoclopramide and tardive dyskinesia," Aliment Pharmacol Ther 2010, 31(1):11-19.
Remington et al., "Tetrabenazine Augmentation in Treatment-Resistant Schizophrenia," Journal of Clinical Psychopharmacology, Feb. 1, 2012, 32(1):95-99.
Robey et al., "Modes and patterns of self-mutilation in persons with Lesch-Nyhan disease," Dev Med Child Neurol. Mar. 2003, 45(3):167-171.
Russian Office Action in Russian Application No. 2016147523, dated Dec. 27, 2018, 18 pages.
Sakimoto et al., "Phenotypic abnormalities in a chorea-acanthocytosis mouse model are modulated by strain background," Biochem Biophys Res Commun., 472(1):118-124.
Santus and Baker, "Osmotic drug delivery: a review of the patent literature," J. Controlled Release, 1995, 35(1)1-21.
Sawant, "Necessity of Establishing Chemical Integrity of Polymorphs of Drug Substance Using a Combination of NMR, HPLC, Elemental Analysis, and Solid-State Characterization Techniques: Case Studies," Organic Process Research & Development 17.3, 2013, :519-532.
Scherman et al., "[3H]dihydrotetrabenazine, a new in vitro monoaminergic probe for human brain," Journal of Neurochemistiy 1988, 50(4):1131-1136.
Schneider et al., "Efficacy and adverse effects of atypical antipsychotics for dementia: meta-analysis of randomized, placebo-controlled trials," Am J Geritr Psychiatiy., 2006, 14(3):191-210.
Schretlen et al., "Behavioral aspects of Lesch-Nyhan disease and its variants," Dev Med Child Neurol., Oct. 2005, 47(10):673-677.
Schretlen et al., "Neurocognitive functioning in Lesch-Nyhan disease and partial hypoxanthine-guanine phosphoribosyltransferase deficiency," J Int. Neuropsychol Soc., 2001, 7:805-812.
Scott et al., Making and Breaking Serotonin Neurons and Autism, Int J Devl Neuroscience., 2005, 23:277-285.
Sever et al., "Process Analytical Technology in Solid Dosage Development and Manufacturing," Developing Solid Oral Dosage Forms Pharmaceutical Theory and Practice, Jan. 2008, 827-841.
Shen et al. "Safety and Efficacy of Tetrabenazine and use of Cocomitant Medications during Long-Term, Open-Label Treatment of Chorea Associated with Huntington's and Other Diseases," Tremor and Other Myperkinetic Movements, Oct. 22, 2013, https://tremoijournal.org/index.php/tremor/article/view/191, pp. 1-12.
Siegert et al., "Efficacy and Safety of Valbenazine (NBI-98854) in Subjects with Tardive Dyskinesia: Results of a Long-Term Study (KINECT 3 Extension)," Poster Presented At The Xxii World Congress On Parkinson's Disease And Related Disorders, Nov. 12-15, 2017, 1 page.
Silverman et al., "Behavioural phenotyping assays for mouse models of autism," Nature Reviews Neuroscience, Jul. 2010, 11(7):490-502.
Simpson et al., "A rating scale for extrapyramidal side effects," Acta Psychiatry Scand Suppl, 1970, 212:11-19.
Singer et al., "Assessing the Effectiveness of Valbenazine in the Treatment of Tardive Dyskinesia as Determined by the AIMS and PGIC: Results from the KINECT 4 Trial," Poster Presented At The 22nd Annual International Congress Of Parkinson's Disease And Movement Disorders, Oct. 5-9, 2018, 1 page.
Skor et al., "Differences in dihydrotetrabenazine isomer concentrations following administration of tetrabenazine and valbenazine," Drugs R D, 2017, 17:449-459.
Smolders et al., "Pharmacokinetics, efficacy, and safety of Hepatitis C virus drugs in patients with liver and/or renal impairment," Drug safety, 2016, 39(7):589-611.
Solon, "Risperidone-reserpine combination in refractory psychosis," Schizophrenia Research, Dec. 1, 1996, 22(3):265-266.
Spencer et al., "Social behavior in Fmr1 knockout mice carrying a human FMR1 transgene," Behave Neurosci., Jun. 2008, 122(3):710-715.
Spina et al., "Effect of fluoxetine on the plasma concentrations of clozapine and its major metabolites in patients with schizophrenia," International Clinical Psychopharmacology, May 1, 1998, 13(3):141-145.
STN CAS RN: 1639208-54-0, entered STN Dec. 22, 2014, 1 page.
Sun et al., "Preparation and evaluation of tetrabenazine enantiomers and all eight stereoisomers of dihydrotetrabenazine as VMAT2 inhibitors," Eur. J. Med. Chem., 2011, 46(5):1841-1848.
Table 14.3.5.14.1, "Young Mania Rating Scale (YMRS) Total Score and Change from Baseline (CFB) Values by Visit and Treatment Group," Neurocrine Biosciences, Inc., Oct. 8, 2015, 6 pages.
Tandon et al., "World Psychiatric Association Pharmacopsychiatry Section Statement on Comparative Effectiveness of Antipsychotics in the Treatment of Schizophrenia," Schizophrenia Research, Mar. 1, 2008, 100(1-3):20-38.
Tarsy and Baldessarini, "Epidemiology of tardive dyskinesia: is risk declining with modern antipsychotics?" Movement Disorders, May 2006, 21(5):589-598.
Tauber et al., "Elevated Levels of the Vesicular Monoamine Transporter and a Novel Repetitive Behavior in the *Drosophila* Model of Fragile X Syndrome," PLoS One, Nov. 11, 6(11):e27100.
Teasdale et al., "Mechanism and Processing Parameters Affecting the Formation of Methyl Methanesulfonate from Methanol and Methanesulfonic Acid: An Illustrative Example for Sulfonate Ester Impurity Formation," Org Process Res. Dev., 2009, 15:13429-433.
Teasdale, "Sulfonate Esters—How Real is the Risk? Summary of Key Findings from PQRI Studies of the Reaction Between Sulfonic acids and Alcohols," 42 pages.
Teasdale, "Sulphonate esters: a real or imagined risk? PQRI studies to determine actual risk," British Pharmaceutical Conference, Manchester Sep. 10-12, 2007, J Pharmacy Pharmacol. A-78, Abstract 218.
Tenback et al, "Incidence and persistence of tardive dyskinesia and extrapyramidal symptoms in schizophrenia," J Psychopharmacol, Jul. 2010, 24(7):1031-1035.
Teng et al., "Lobeline displaces [3H]dihydrotetrabenazine binding and releases [3H]dopamine from rat striatal synaptic vesicles: comparison with d-amphetamine," J Neurochem. 1998, 71(1):258-265.
Thai-Curato et al., "Cardiovascular profile of valbenazine: analysis of pooled dated from three randomized, double-blind, placebo-controlled trials," Drug Safety, 2017, 41(4):429-440.
Tian et al., "CYP3A4-mediated pharmacokinetic interactions in cancer therapy," Curr. Drug Metab., 2014, 15(8):808-17.
Tomemori et al., "A gene-targeted mouse model for chorea-acanthocytosis," J Neurochem, 2005, 92(4):759-766.

(56) References Cited

OTHER PUBLICATIONS

Traynor, "Valbenazine approved for treatment of tardive dyskinesia," ASHP, Apr. 17, 2017, retrieved from URL: https://www.ashp.org/news/2017/04/17/valbenazine-approved-for-treatment-of-tardive-dyskinesia?loginreturnUrl=SSOCheckOnly, retrieved on Jun. 22, 2020, 3 pages.
Tsoussis et al., "Disclosure of cancer diagnosis: the Greek experience," JBUON, Open Access Journal aimed at the rapid diffusion of scientific knowledge in Oncology, 2013, 18(2):516-526.
United States Pharmacopoeia ("USP"), "Bulk Density and Tapped Density of Powders," <616>, 2015, 3 pages.
United States Pharmacopoeia ("USP"), "Disintegration," <701>, 2016, 4 pages.
United States Pharmacopoeia ("USP"), "Dissolution," <711>, 2011, 8 pages.
United States Pharmacopoeia ("USP"), "Uniformity of Dosage Units," <905>, 2016, 9 pages.
United States Pharmacopoeia, "Light Diffraction Measurement of Particle Size," <429>, 2016, 8 pages.
US Department of Health and Human Services, and Food and Drug Administration, "Size, Shape, and Other Physical Attributes of Generic Tablets and Capsules," Jun. 2015, 10 pages.
Verkerk et all., "Identification of a gene (FMR-1) containing a CGG repeat coincident with a breakpoint cluster region exhibiting length variation in fragile X syndrome," Cell, May 1991, 65(5):905-914.
Verma et al., "Formulation aspects in the development of osmotically controlled oral drug delivery systems," J. Controlled Release, Feb. 19, 2002, 79(1-3):7-27.
Verma et al., "Osmotically controlled oral drug delivery," Drug Development and Industrial Pharmacy, Jul. 2000, 26(7):695-708.
Wade, "Deuterium isotope effects on noncovalent interactions between molecules," Chem Biol Interact., Feb. 1999, 117(3):191-217.
Watts et al., "Clinical and biochemical studioes on treatment of Lesch-Nylan Syndrome," Archives of Disease in Childhood., 1974, 49:693-702.
Weihe and Eiden, "Chemical neuroanatomy of the vesicular amine transporters.," The FASEB Journal, Dec. 2000, 14(15):2435-2449.
Wermuth et al., "The practice of medicinal chemistry part II," Technomics, 1999, 347-365.
Woods et al, "Incidence of tardive dyskinesia with atypical versus conventional antipsychotic medications: a prospective cohort study," J Clin Psychiatry, Apr. 2010, 71(4):463-474.
Yamashita et al., "Modeling of rifampicin-induced CYP3A4 activation dynamics for the prediction of clinical drug-drug interactions in vitro data," PLoS One, 2013, 8(9):e70330, 11 pages.
Yasumoto et al., "Inhibitory effect of selective serotonin reuptake inhibitors on the vesicular monoamine transporter 2," Neuroscience Letters, May 1, 2009, 454(3):229-232.
Zello et al., "Plasma and urine enrichments following infusion of L-[1-13C]phenylalanine and L-[ring-2H5]phenylalanine in humans: evidence for an isotope effect in renal tubular reabsorption," Metabolism, 1994, 43(4):487-491.
Zhang et al, "Synergistic Effects of Olanzapine and other Antipsychotic Agents in Combination with Fluoxetine on Norepinephrine and Dopamine release in rate Prefrontal Cortex," Neuropsychopharmacology, Sep. 1, 2000, 23(3):250-262.
[No Author Listed], "Blenrep (belantamab mafodotin-blmf) Highlights of Prescribing Information," GlaxoSmithKline, Aug. 2020, 23 pages.
[No Author Listed], "Crestor (rosuvastatin calciu) Highlights of Prescribing Information," AstraZeneca Pharmaceuticals, May 2016, 35 pages.
[No Author Listed], "Iclusig (ponatinib) Highlights of Prescribing Information," ARIAD Pharmaceuticals, Inc., Dec. 2012, 17 pages.
[No Author Listed], "Invokana (canagliflozin). Highlights of Prescribing Information," Janssen Pharmaceuticals, Inc., Oct. 2018, 50 pages.
[No Author Listed], "Summary of Changes" Neurocrine Biosciences, Inc., Nov. 6, 2020, 4 pages.

[No Author Listed], "Veklury (remdesivir) Highlights of Prescribing Information," Gilead Sciences, Inc., Oct. 2020, 30 pages.
[No Author Listed], "Zepzelca (lubrinectedin) Highlights of Prescribing Information," Jazz Pharmaceuticals, Inc., Jun. 2020, 16 pages.
[No Author Listed], "Zocor (simvastatin) Highlights of Prescribing Information," Merck Sharpe & Dohme Corp., Sep. 2020, 22 pages.
Alexander et al., "Increased aggression in males in transgenic Tg2576 mouse model of Alzheimer's disease," Behav Brain Res., 2011, 216(1):77-83.
Center for Drug Evaluation and Research Application No. 2092410 ("Publication No. 2092410"), Clinical Pharmacology and Biopharmaceuticals Review, Jun. 1, 2017, 297 pages.
Citrome, "Reprint of: Clinical management of tardive dyskinesia: five steps to success," Journal of Neurological Sciences, 2018, 389:61-66.
Citrome, "Valbenazine for tardive dyskinesia: A systematic review of the efficacy and safety profile for this newly appolved novel medication—What is the number needed to treat, number needed to harm and likelihood to be helped or harmed?," Int J Clin Pract., 2017, e12964.
Harris Interactive Inc. for Schwarz Pharma, 2003, Pill-Swallowing Problems in America: A National Survey of Adults. 1-39.
Hassan et al., "Drug use and dosing in chronic kidney disease," Annals of the Academy of Medicine, 2009, 38(12):1095-1103.
Tauber et al., "Elevated Levels of the Vesicular Monoamine Transporter and a Novel Repetitive Behavior in the *Drosophila* Model of Fragile X Syndrome," PLoS One, Nov. 2, 2011, 6(11):e27100.
Teasdale, "Sulfonate Esters—How Real is the Risk? Summary of Key Findings from PQRI Studies of the Reaction Between Sulfonic acids and Alcohols," Product Quality Research Institute, 2007, 42 pages.
U.S. Appl. No. 17/007,710, filed Aug. 31, 2020, Liang et al.
U.S. Appl. No. 17/125,190, filed Dec. 17, 2020, O'Brien et al.
Anderson and Flora, "Perparation of Water Soluble Compounds Through Salt Formation," The Practice of medicinal chemistiy part II, Wermuth ed., 1999, 34:739-754.
Aranda et al., "Synthesis and biological activity of iodinated and photosensitive derivatives of tetrabenazine," Eur J Med Chem., May 1990, 25:369-374.
Brittain, "Polymorphism in pharmaceutical solids," Informa Healthcare, 2009, 2:1-229.
Fallgatter Andreas et al., "22q11.2 deletion syndrome as a natural model for COMT haploinsufficiency-related dopaminergic dysfunction in ADHD," Int. J. Neuropsychopharmacology, 2007, 10(3):295-299.
Josiassen, "Successful Treatment of Severe Tardive Dyskinesia with Valbenazine, Including a Patient's Perspective," American Journal of Case Reports, 2017, 18:1185-1189.
Lu, "Stereoselectivity in drug metabolism," Expert Opinion on Drug Metabolism & Toxicology, 2007, 3(2):149-158.
Kaminsky & Zhang, "Human P450 metabolism of warfarin," Pharmacol Ther., 1997, 73(1):67-74.
Kaur et al., "Tetrabenazine: Spotlight on Drug Review," Annals of Neuroscience, 2016, 23:176-185.
Material Safety Data Sheet. Product Name Valbenazine tosylate. Published May 1, 2014 (see Revision date). Retrieved from internet May 23, 2020. URL: https://www.selleckchem.com/msds/MSDS_S9500.pdf, 2 pages.
Selvi et al., "The comparison of aripiprazole and risperidone augmentation in selective serotonin reuptake inhibitor-refractory obsessive-compulsive disorder: a single-blind, randomised study," Hum Psychopharnnacol Olin Exp., 2011, 26:51-57.
Smith et al., "Effect of Paroxetine on the Pharmacokinetics of Valbenazine and its active Metaolite," PowerPoint presentation presented virtually at the American Academy of Neurology, May 2020, 10 pages.
United States Pharmacopeia general chapter on XRPD, USPPF, Retrieved from URL: https://www.usp.org/sites/default/files/usp/document/harmonization/genchapter/g14_pf_35_3_2009.pdf, 2016, 11 pages.

(56) References Cited

OTHER PUBLICATIONS

Yorulmaz et al., "OCD cognitions and symptoms in different religious contexts," Journal of Anxiety Disorders, Apr. 2009,23(3):401-406.
Bauer, "Polymorphism-A Critical Consideration in Pharmaceutical Development, Manufacturing, and Stability," Journal of Validation Technology., 2008, pp. 15-23.
Fary, "Top New Drug Approvals of 2018," Caring for the Ages, 2018, 19(12):7-9.
PCT International Preliminary Report on Patentability in International Appln. No. PCT/US2020/032188, dated Nov. 2, 2021, 14 pages.
Remington et al., "Safety and Tolerability of Valbenazine (NBI-98854) in Subjcts with Tardive Dyskinesia: Results of Long-Term Exposure Data From Three Studies," Neuropsychopharmacology, Dec. 5, 2016, 41:S212-S213.
U.S. Appl. No. 16/662,346, McGee et al., Valbenazine Salts and Polymorphs Thereof, filed Oct. 24, 2019, 115 pages.
Argawal et al., "An overview of transporter information in package inserts of recently approved new molecular entities," Pharm. Res., 2013, 30:899-910.
Babu, "Impurity Profiling of Drug Substances in Pharmaceuticals: Pharmaceutical Guidelines," 2012 [retrieved on Oct. 7, 2021], retrieved from URL <https://www.pharmaguideline.com/2012/10/impurity-profiling-of-drug-substances.html>, 5 pages.
Byrn et al., "Pharmaceutical Solids: A Strategic Approach to Regulatory Considerations," Pharmaceutical Research, 1995, 12(7):945-954.
Carstensen, "Effect of Moisture on the Stability of Solid Dosage Forms," Oct. 20, 1988, 14(14):1927-1969.
Chen and Raymond, "Roles of rifampicin in drug-drug interactions: underlying molecular mechanisms involving the nuclear pregnane X receptor," Ann Clin Microbial Antimicrob., Feb. 2006, 5(3):1-11.
Citrome, "Breakthrough Drugs for the Interface Between Psychiatry and Neurology," Int J Clin Prac., Apr. 2016, 70(4):298-299.
Clinicaltrials.gov, "Safety and Tolerability of NBI-98854 for the Treatment of Tardive Dyskinesia (Kinect 4)," NCT02405091, dated Apr. 1, 2015, retrieved from URL <https://www.clinicaltrials.gov/ct2/show/NCT02405Q91>, 32 pages.
Clinicaltrial.gov, "Study to assess the effect of ketoconazole on the pharmacokinetics of NBI-98854 in healthy subjects" NCT01910480, dated Sep. 2013, retrieved from URL <https://clinicaltrials.gov/ct2/show/study/NCT0191048Q>, 13 pages.
ClinicalTrial.gov "A Phase 3 Study of NBI-98854 for the Treatment of Tardive Dyskinesis (Kinect 3)," NCT02274558, dated Oct. 2014, retreived from URL <https://clinicaltrials.gov/ct2/show/NCT02274558>, 31 pages.
ClinicalTrial.gov, "Safety, Tolerability, and Pharmacokinetics of a Single Dose of NBI-98854 in Subjects with Mild, Moderate, or Severe Hepatic Insufficiency," NCT01916993, dated Aug. 6, 2013, retreived from URL <https://clinicaltrials.gov/ct2/show/NCT01916993>, 13 pages.
ClinicalTrial.gov, "NBI-98854 Dose Titration Study for the Treatment of Tardive Dyskinesia," NCT01733121, Nov. 26, 2012, retreived from URL <https://clinicaltrials.gov/ct2/show/NCT01733121>, 30 pages.
Collman et al., "Comparison of a rational vs. high throughput approachfor rapid salt screening and selection," Drug Dev Ind Pharm., Jan. 2013, 39:29.
Digoxin, Center for Drug Evaluation and Research: Labeling, Roxane Laboratories, Inc., Aug. 2004, 9 pages.
Lanoxin, Highlights of Prescribing Information, Covis Pharmaceuticals, Inc., 2013, 22 pages.
No Author, "Guidance on the Investigation of Drug Interactions," European Medicines Agency, Jun. 2012, 59 pages.
No Author, "Guideline on the Evaluation of the Pharmacokinetics of Medicinal Products in Patients with Impaired Hepatic Function," European Medicines Agency, Feb. 17, 2005, 10 pages.
Ex parte DeCastro, 28 USPQ2d (BNA) 1391, Appeal No. 92-3899, Mar. 23, 1993, 5 pages.
No Author, "Guideline for Submitting Supporting Documentation in Drug Applications for the Manufacture of Drug Substances," US Food & Drug Administration, Feb. 1987, 48 pages.
No Author, "Guidance For Industry: Q3C Impurities: Residual Solvents," US Food & Drug Administration, Dec. 1997, 16 pages.
No Author, "Guidance for Industry Pharmacokinetics in Patients with Impaired Renal Function—Study Design, Data Analysis, and Impact on Dosing and Labeling," US Food and Drug Administration, May 1998, 19 pages.
No Author, "FDA Guidance for Industry, ANDAs: Impurities in Drug Substances," US Food and Drug Administration, Nov. 1999, 19 pages.
No Author, "Guidance for Industry: Immunotoxicology Evaluation of Investigational New Drugs," US Food and Drug Administration, Oct. 2002, 38 pages.
No Author, "Guidance for Industry: Q3A Impurities in New Drug Substances," US Food and Drug Administration, Jun. 2008, 17 pages.
No Author, "Draft Guidance for Drug Interaction Studies-Study Design, Data Analysis, Implications for Dosing, and Labeling Recommendations," US Food & Drug Administration, Feb. 2012, 79 pages.
No Author, "Guidance for Industry, Clinical Pharmacogenomics: Premarket evaluation in Early-Phase Clinical Studies and Recommendations for Labelling," US Food & Drug Administration, Jan. 2013, 26 pages.
No Author, "Guidance for Industry-Pharmacokinetics in Patients with Impaired Hepatic Function: Study Design, Data Analysis, and Impact on Dosing and Labeling," US Food & Drug Administration, May 2003, 19 pages.
No Author, "Guidance for Industry: Drug Interaction Studies-Study Design, Data Analysis. and Implications for Dosing and Labeling," US Food & Drug Administration, Sep. 2006, 55 pages.
No Author, "Guidance for Industry: Pharmacokinetics in Patients with Impaired Hepatic Function: Study Design, Data Analysis, and Impact on Dosing and Labeling," FDA's Guidance for Industry, US Food & Drug Administration, May 2003, 19 pages.
No Author, "FDA Guidance for Industry: Q3A Impurities in New Drug Substance," FDA's Guidance for Industry, US Food & Drug Administration, Aug. 2006, 18 pages.
Fernandez Casares et al., "An evaluation of salt screening methodologies," J Pharm., Jun. 2015, 67:812-822.
Fessenden & Fessenden, "Crystallization," Organic Laboratory Techniques, Brooks/Cole Publishing Co., 1993, 2nd Edition, pp. 38-54.
Finch et al., "P-glycoprotein and its role in drug-drug interactions," Australian Prescriber, 2014,37:137-139.
No Author, "Guidance for Industry on Drug Interaction Studies: Study Design, Data Analysis, and Implications for Dosing and Labeling Availability," Federal Registry, Sep. 12, 2006, 71(176):53696-53697.
Gu et al., "Polymorph Screening: Influence of Solvents on the Rate of Solvent Mediated Polymorphic Transformation," J Pharm Sci., 2001, 90(11): 1878-1890.
Hilfiker et al., "Polymorphism—Integrated Approach From High-Throughput Screening to Crystallization Optimization," J Therm Anal Cal., 2003, 73:429-440.
Hoeft, "An overview of clinically significant drug interactions between medications used to treat psychiatric and medical conditions," Mental Health Clinician, May 2014, 4(3): 118-130.
Hosking et al., "Linkage disequilibrium mapping identifies a 390 kb region associated with CYP2D6 poor drug metabolising activity," Pharmacogenomics J., 2002, 2:165-175.
No Author, "Impurities: Guideline for Residual Solvents," European Medicines Agency, Feb. 2009, 22 pages.
No Author, "Specifications: Test Procedures and Acceptance Criteria for New Drug Substances and Drug Products: Chemical Substances Q6A," ICH Harmonized Tripartite Guideline, Oct. 6, 1999, 35 pages.
No Author, "Impurites in New Drug Substances Q3A(R2)," ICH Harmonized Tripartite Guideline, Oct. 25, 2006, 15 pages.
Kanojia et al., "Modified Excipients in Novel Drug Delivery: Need of the Day," JPTRM., 2013, 1:81-107.

(56) References Cited

OTHER PUBLICATIONS

Kapil et al., "Effects of Paroxetine, a CYP2D6 Inhibitor, on the Pharmacokinetic Properties of Hydrocodone After Coadministration With a Single-entity, Once-daily, Extended-release Hydrocodone Tablet," Clin Then, 2015, 37(10):2286-2296.
Lanoxin, Prescribing Information, GlaxoSmithKline, Aug. 2009, 18 pages.
Isidro-Llobet et al., "Amino Acid-Protecting Groups," Chemical Reviews, 2009, 109(6):2455-2504.
Lupin, Highlights of Prescribing Information, Lupin Pharmaceuticals, Inc., Apr. 2018, 27 pages.
Lynch, "The Effect of Cytochrome P450 Metabolism on Drug Response, Interactions, and Adverse Effects," American Family Physician, Aug. 2007, 76(3):391-396.
Mahatthanatrakul, "Rifampin, a cytochrome P450 3A inducer, decreases plasma concentrations of antipsychotic risperidone in healthy volunteers," Journal of Clinical Pharmacy and Therapeutics, 2007, 32:161-167.
Martin et al., "Effects of CYP3A4 Inhibitors Ketoconazole and Verapamil and the CYP3A4 Inducer Rifampicin on the Pharmacokinetic Parameters of Fostamatinib: Results from In Vitro and Phase I Clinical Studies," Drugs RD, 2016, 16:81-92.
Miller et al., "Identifying the Stable Polymorph Early in the Drug Discovery Development Process," Pharm Dev & Tech., 2005, 10:291-297.
Mohrig et al., "Technique 9: Recrystallization," Techiques in Organic Chemistry, W.H. Freeman and Co., 2003, pp. 78-93.
Mora et al., "CYP450 and Its Implications in the Clinical Use of Antipsychotic Drugs", Clin Exp Pharmacol., 2015, 5(3)4 000176.
Morissette et al., "High-Throughput Crystallization: Polymorphs, Salts, Co Crystals and Solvates of Pharmaceutical Solids," Adv Drug Deliv Rev., 2004, 56(3):275-300.
Mutalik et al., "Review of Drug Interactions: A Comprehensive Update," British J of Pharm Res., 2014, 4(8):954-980.
Nair et al., "A simple practice guide for dose conversion between animals and human," J of Basic and Clin Pharm,, 2016, 7(2):27-31.
Nitoman, Product Monograph, Valeant Canada LP, Mar. 21, 2011, 17 pages.
Noxafil, Highlights of Prescribing Information, Merck & Co., Inc., dated Jul. 2021, 43 pages.
Ohno et al., "General Framework for the Prediction of Oral Drug Interactions Caused by CYP3A4 Induction from In Vivo Information," Clin Pharmacokinet., 2008, 47(10):669-680.
Wadekar et al., "Evaluating Impurities in Drugs (Part III of III)," PharmTech., Apr. 2, 2012, 36(4):76-86.
Poon et al., "Role of Tetrabenazine for Huntington's Disease-Associated Chorea,"The Annals of Pharmacotherapy, 2010, 44:1080-1089.
No Author, "Neurocrine Biosciences Announces Additional European and United States Patents Issued on Proprietary VMAT2 Inhibitor" Jan. 23, 2013, 1 page.
No Author, "Neurocrine Announces Positive Results of VMAT2 Inhibitor NBI-98854 in Kinect 2 Study," Neurocrine Biosciences, Jan. 6, 2014, 3 pages.
No Author, "Neurocrine Announces Initiation of Phase III Study for VMAT2 Inhibitor NBI-98854" Neurocrine Biosciences, Oct. 20, 2014, 2 pages.
No Author, "Neurocrine Announces Positive Results from Phase III Kinect 3 Study of NBI-98854 in Tardive Dyskinesia," Neurocrine Biosciences, Oct. 8, 2015, 2 pages.
No Author, "Neurocrine Announces Phase Jib Results of VMAT2 Inhibitor NBI-98854 for Treatment of Tardive Dyskinesia," Sep. 9, 2013, 3 pages.
Richardson et al., "Efficacy of the Branched-Chain Amino Acids in the Treatment of Tardive Dyskinesia in Men," Am J Psychiatry., Jun. 2003, 160(6):1117-1124.
Riedl et al., "Adverse Drug Reactions: Types and Treatment Options," Am Family Physician., Nov. 2003, 68(9): 1781-1790.
PubChem.gov, "Rifampicin," received on Oct. 7, 2021, received from URL <https://pubchem.ncbi .nlm.nih.gov/ compound/ Rifampicin>, 64 pages.
Shah et al., "Recent Approaches of "Impurity Profiling" In Pharmaceutical Analysis: A Review," Int J Pharm Sci and Res., 2012, 3(10):3603-3617.
Song et al., "Amino Acid Ester Prodrugs of the Anticancer Agent Gemcitabine: Synthesis, Bioconversion, Metabolic Bioevasion, and hPEPTl-Mediated Transport," Molecular Pharmaceutics, 2005, 2(2):157-167.
Staal et al., "Interactions of J-methyl-4-phenylpyridinium and other compounds with P Glycoprotein: relevance to toxicity of l-methyl-4-phenyl- J,2,3,6- tetrahydropyridine," Brain Res., 2001, 910(1-2): 116-125.
No Author, "Loss on Drying," US Pharmacopeia 35: Physical Tests, May 1, 2012, 731:317-318.
Verbeeck, "Pharmacokinetics and dosage adjustment in patients with hepatic dysfunction," Eur J Clin Pharmacol., 2008, 64:1147-1161.
Wade Jr et al., "Amino Acids, Peptides, and Proteins," Organic Chemistry Prentice Hall, Inc., 1995, 3rd Ed., Chapter 24, pp. 1164-1210.
Waterman, "The Application of the Accelerated Stability Assessment Program (ASAP) to Quality by Design (QbD) for Drug Product Stability," AAPS PharmSciTech, Sep. 2011, 12(3):932-937.
Xenazine, Highlights of Prescribing Information, Recipharm Fontaine SAS, May 2011, 42 pages.
Xenazine, Highlights of Prescribing Information, Prestwick Pharmaceuticals, Inc., May 2008, 63 pages.
Yao et al., "Preparation and evaluation of tetrabenazine enantiomers and all eight stereoisomers of dihydrotetrabenazine as VMAT2 inhibitors," European Journal of Medicinal Chemistry, 2011, 46(5):1841-1848.
Yu et al., "Key Findings from Preclinical and Clinical Drug Interaction Studies Presented in New Drug and Biological License Applications Approved by the Food and Drug Administration in 2014," Drug Metabolism and Disposition, Jan. 2016, 44(1):83-101.
Zhang et al. "Predicting Drug-Drug Interactions: An FDA Perspective," AAPS Journal, Jun. 2009, 11(2)300-306.
Complaint, *Neurocrine Biosciences Inc.* v- *Crystal Pharmaceutical (Suzhou) Co., Ltd. et al.*, U.S. District Court for the District of Delaware. Civ. Action No. 1:21-cv-01464-MN (Oct. 18, 2021).
Complaint, *Neurocrine Biosciences Inc.* v- *Lupin Limited et al.*, U.S. District Court for the District of Delaware. Civ. Action No. 1:21-cv-01408-MN (Oct. 1, 2021).

* cited by examiner

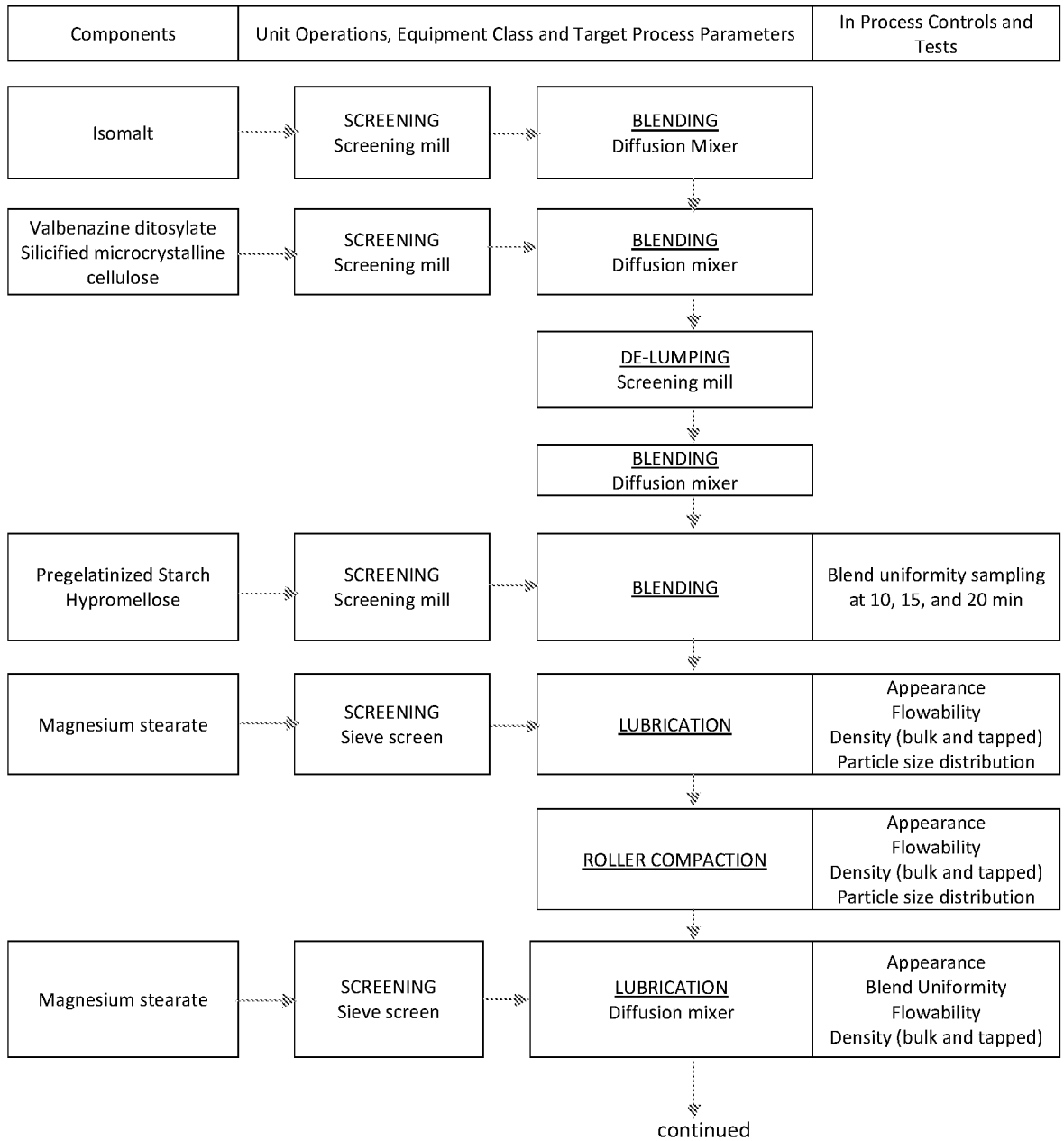

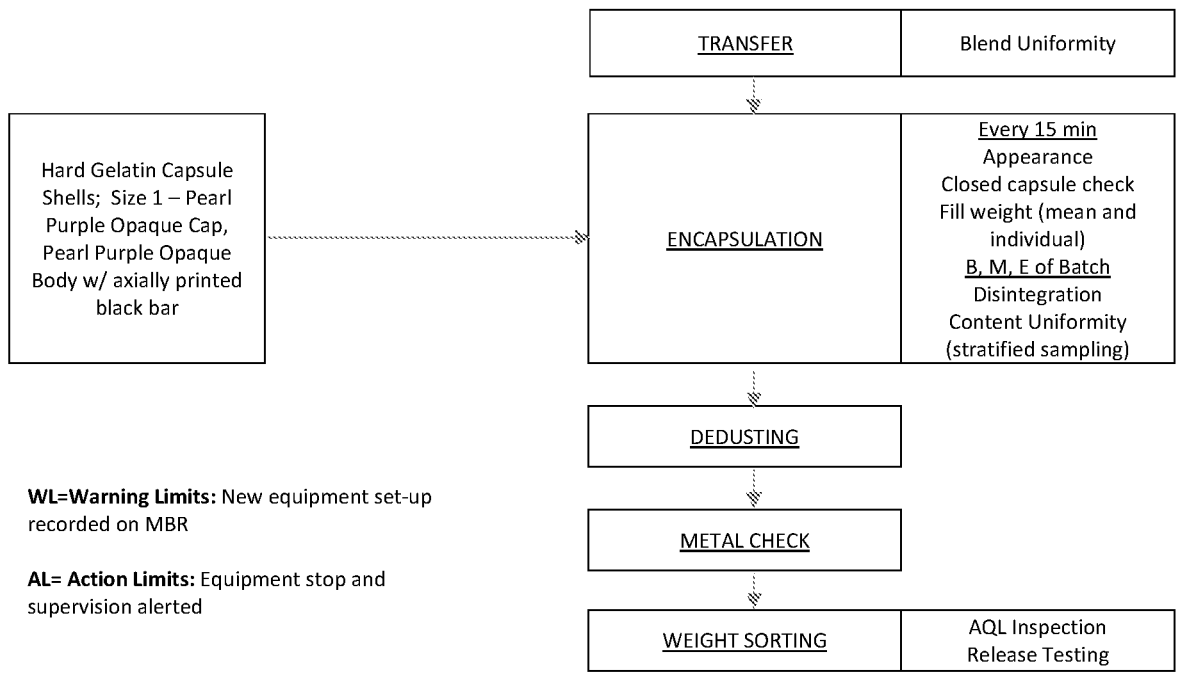

HIGH DOSAGE VALBENAZINE FORMULATION AND COMPOSITIONS, METHODS, AND KITS RELATED THERETO

BACKGROUND

Technical Field

This invention related to a novel pharmaceutical composition of L-Valine, (2R,3R,11bR)-1,3,4,6,7,11b-hexahydro-9,10-dimethoxy-3-(2-methylpropyl)-2H-benzo[a]quinolizin-2-yl ester (referred to herein as "valbenazine") and pharmaceutically acceptable salts, as well as to compositions, method, and kits relating to the same.

Description of the Related Art

Dysregulation of dopaminergic systems is integral to several central nervous system (CNS) disorders, including neurological and psychiatric diseases and disorders. These neurological and psychiatric diseases and disorders include hyperkinetic movement disorders, and conditions such as schizophrenia and mood disorders. The transporter protein vesicular monoamine transporter-2 (VMAT2) plays an important role in presynaptic dopamine release and regulates monoamine uptake from the cytoplasm to the synaptic vesicle for storage and release.

Despite the advances that have been made in this field, there remains a need for new therapeutic products useful to treatment of neurological and psychiatric diseases and disorders and other related diseases or conditions described herein. One such promising agent is valbenazine. The free base form of valbenazine has the following chemical structure:

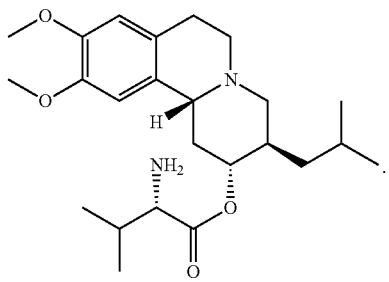 [SMILES: COc1cc2c(cc1OC)[C@H]1C[C@@H](OC(=O)[C@@H](N)C(C)C)[C@H](CC(C)C)CN1CC2]

Many different factors are considered in the selection of a counter-ion for the formation of a salt. Only the 4-toluenesulfonate salt had the combination of properties that made it a developable form of valbenazine. A formulation of valbenazine:4-toluenesulfonate (1:2) (referred to herein as "valbenazine ditosylate") has been previously reported in the FDA approved drug label for valbenazine ditosylate (Ingrezza®). It is manufactured in the form of size 1 hard gelatin capsule for a 40 mg unit dosage, as measured as the free base.

With an increase in dose, the high molecular weight of two 4-toluenesulfonic acid counter-ions in the salt form of valbenazine creates a unique challenge to develop a formulation with acceptable powder flow properties. The prior art does not provide for valbenazine or valbenazine ditosylate in a form suitable for solid-dosing at preferred high loading drug levels, particularly with regard to capsule formation. Therapeutically acceptable capsules according to the known formulation and procedure containing more than about 30% valbenazine ditosylate were not manufacturable. Single dosage units are unavailable to patients in need of high doses of valbenazine Many patients experience difficulty swallowing tablets and capsules. This problem can lead to a variety of adverse events and patient noncompliance with treatment regimens. A survey of adults on difficulties swallowing tablets and capsules suggests that this problem may affect as many as 40 percent of Americans. (Harris Interactive Inc. for Schwarz Pharma, 2003, Pill-Swallowing Problems in America: A National Survey of Adults. 1-39.) Individuals who find it difficult to swallow tablets and capsules frequently cite the size as the main reason for the difficulty in swallowing. (Fields, J. et al., Pill Properties that Cause Dysphagia and Treatment Failure, *Curr. Ther. Res. Clin. Exp.*, 2015, 77:79-82.)

Larger tablets and capsules have also been shown to affect the transit of drug products through the pharynx and esophagus. Larger tablets and capsules have been shown to have a prolonged esophageal transit time and may directly affect a patient's ability to swallow a particular drug product. This can lead to disintegration of the product in the esophagus and/or cause injury to the esophagus. The United States Food and Drug Administration ("FDA") has indicated "that size should be considered as part of a single product risk/benefit profile." (FDA Guidance for Industry on *Size, Shape, and Other Physical Attributes of Generic Tablets and Capsules* at 5, 1-7, June 2015.) The FDA further recommends "that the largest dimension of a tablet or capsule should not exceed 22 mm and that capsules should not exceed a standard 00 size." Id.

There remains a substantial need for improved techniques and products for the oral administration of valbenazine, or a pharmaceutically acceptable salt thereof, to patients in need thereof, including patients having neurological and psychiatric diseases and disorders such as hyperkinetic movement disorders, schizophrenia, and mood disorders The present disclosure fulfills these and other needs, as evident in reference to the following disclosure.

BRIEF SUMMARY

The present invention generally provides a novel solid drug form of valbenazine or valbenazine ditosylate, as well as to compositions, methods, and/or kits for oral administration of the same.

Valbenazine has particular utility in the treatment of hyperkinetic movement disorders, including tardive dyskinesia and other conditions as described in greater detail below. The solid drug form of valbenazine provided herein provides for high loading capacity, thus allowing formulations of valbenazine in a form suitable for oral dosing. In some embodiments, the solid drug form is a solid pharmaceutical composition. In some embodiments, the solid drug form is a unit dosage form. In some embodiments, the solid drug form is a solid composition.

In one embodiment a solid pharmaceutical composition is provided of valbenazine, or a pharmaceutically acceptable salt thereof, silicified microcrystalline cellulose, isomalt, hydroxypropyl methylcellulose, partially pregelatinized maize starch, and magnesium stearate. In one embodiment, the pharmaceutically acceptable salt is valbenazine ditosylate.

In another embodiment, a unit dosage form of a pharmaceutical composition is provided having a capsule of size 1 or smaller and at least 80 mg of valbenazine, or a pharmaceutically acceptable salt thereof, as measured as the free base.

In another embodiment, a unit dosage form of a pharmaceutical composition is provided having a capsule of size 2 or smaller and at least 20 mg of valbenazine, or a pharmaceutically acceptable salt thereof, as measured as the free base. In one embodiment, the unit dosage form has at least 40 mg of valbenazine, or a pharmaceutically acceptable salt thereof, as measured as the free base.

In one embodiment, a unit dosage form of a pharmaceutical composition is provided having a capsule of size 0 or smaller and at least 120 mg of valbenazine, or a pharmaceutically acceptable salt thereof, as measured as the free base.

In another embodiment, a unit dosage form of a pharmaceutical composition is provided with valbenazine ditosylate having a w/w % of at least 35%.

In one embodiment, a unit dosage form of a pharmaceutical composition is provided with valbenazine ditosylate having a w/w % of about 40%, silicified microcrystalline cellulose having a w/w % of about 25%, isomalt having a w/w % of about 20%, hydroxypropyl methylcellulose having a w/w % of about 5%, partially pregelatinized maize starch having a w/w % of about 7.5%, and magnesium stearate having a w/w % of about 2.5%.

In one embodiment is provided a method of orally administering a unit dosage form valbenazine or valbenazine ditosylate to a subject in need thereof.

In one embodiment is provided a method for treating a hyperkinetic movement disorder in a patient in need thereof by administering to the patient a therapeutically effective amount of the solid drug form of valbenazine or valbenazine ditosylate.

In one embodiment is provided a method for treating a hyperkinetic movement disorder in a patient in need thereof by administering to the patient a therapeutically effective amount of the solid pharmaceutical composition of valbenazine or valbenazine ditosylate.

In one embodiment, a kit is provided with a plurality of oral unit dosage forms of a solid pharmaceutical composition of valbenazine or valbenazine ditosylate in combination with instructions for administration.

In one embodiment, a kit is provided with a plurality of oral unit dosage forms of a solid composition of valbenazine or valbenazine ditosylate in combination with instructions for administration.

In one embodiment, a method for producing a unit dosage form of valbenazine ditosylate is provided.

In one embodiment, a composition is provided of valbenazine, or a pharmaceutically acceptable salt thereof, silicified microcrystalline cellulose, isomalt, hydroxypropyl methylcellulose, partially pregelatinized maize starch, and magnesium stearate.

Also provided is a solid composition of valbenazine, or a pharmaceutically acceptable salt thereof, and at least one pharmaceutically acceptable excipient, wherein the solid composition has a bulk density of at least about 0.5 mg/mL.

Also provided is a solid composition of valbenazine, or a pharmaceutically acceptable salt thereof, and at least one pharmaceutically acceptable excipient, wherein the solid composition has a tapped density of at least about 0.6 mg/mL.

Also provided is a solid composition of valbenazine, or a pharmaceutically acceptable salt thereof, and at least one pharmaceutically acceptable excipient, wherein the solid composition has a d(0.9) particle size distribution less than 100 μm.

Also provided is a solid composition of valbenazine, or a pharmaceutically acceptable salt thereof, and at least one pharmaceutically acceptable excipient, wherein the solid composition has a blend uniformity between about 90% and about 110% with a relative standard deviation of the blend uniformity of less than about 2%.

A solid composition of valbenazine, or a pharmaceutically acceptable salt thereof, and at least one pharmaceutically acceptable excipient, wherein the solid composition has a blend uniformity between about 90% and about 110% with a standard deviation of the blend uniformity of less than about 2%.

Also provided is a process for preparing a unit dosage form comprising valbenazine, or a pharmaceutically acceptable salt thereof, wherein the process comprises:

encapsulating the solid composition described herein, to produce the unit dosage form comprising valbenazine, or a pharmaceutically acceptable salt thereof.

Also provided is a process for preparing a unit dosage form comprising valbenazine, or a pharmaceutically acceptable salt thereof, wherein the process comprises:

encapsulating a lubricated blend to produce a solid composition comprising valbenazine, or a pharmaceutically acceptable salt thereof, wherein the lubricated blend comprises granules of valbenazine, or a pharmaceutically acceptable salt thereof, and at least one lubricant.

Also provided is a unit dosage form, for use in a method of treating a neurological or psychiatric disease or disorder of a patient in need thereof.

Also provided is a solid pharmaceutical composition comprising:

valbenazine, or a pharmaceutically acceptable salt thereof;
at least one water insoluble filler;
at least one water soluble diluent;
at least one binder;
at least one disintegrant; and
at least one lubricant.

Also provided is a unit dosage form of a pharmaceutical composition comprising:

valbenazine ditosylate having a w/w % of about 40%;
at least one water insoluble filler having a w/w % of about 25%;
at least one water soluble diluent having a w/w % of about 20%;
at least one binder having a w/w % of about 5%;
at least one disintegrant having a w/w % of about 7.5%; and
at least one lubricant having a w/w % of about 2.5%.

These and other aspects of the invention will be apparent upon reference to the following detailed description. To this end, various references are set forth herein which describe in more detail certain background information, procedures, compounds, and/or compositions, and are each hereby incorporated by reference in their entirety.

BRIEF DESCRIPTION OF THE SEVERAL VIEWS OF THE DRAWINGS

FIG. 1 shows a process flow diagram for the production of high drug loading valbenazine capsules.

DETAILED DESCRIPTION

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

As used herein, "about" means ±20% of the stated value, and includes more specifically values of ±10%, ±5%, ±2% and ±1% of the stated value.

Hyperkinetic movement disorders represent a category of neurological disorders that are characterized by unwanted and uncontrollable, or poorly controllable, involuntary movements. The phenomenology of these disorders is quite variable encompassing chorea, tremor, dystonia, myoclonus, tics, other dyskinesias, jerks and shakes. Hyperkinetic movement disorders include ataxia, chorea, dystonia, hemifacial spasm, Huntington's disease, chorea associated with Huntingon's disease, myoclonus, restless leg syndrome, tardive dyskinesia, tics, Tourette's syndrome, and tremors.

Mood disorders represent a category of mental disorders in which the underlying problem primarily affects a person's persistent emotional state (their mood). Mood disorders include: major depressive disorder (also called major depression), bipolar disorder, persistent depressive disorder (long lasting low grade depression), cyclothymia (a mild form of bipolar disorder), catatonic depression, post-partum depression, mania, and seasonal affective disorder (SAD). Mood disorders include substance-induced mood disorders and mood disorders due to a medical condition, e.g., hypothyroidism or Parkinson's disease.

Bipolar disorder, also known as bipolar affective disorder or manic-depressive illness, is a mental disorder characterized by periods of elevated mood and periods of depression. The periods of elevated mood is known as mania or hypomania depending on the severity or whether psychosis is present. Symptoms of mania or a manic episode include a long period of feeling "high" or an overly happy or outgoing mood, extreme irritability, talking very fast, racing thoughts, jumping from one idea to another, being easily distracted, increasing activities, being overly restless, sleeping little, having an unrealistic belief in one's abilities, impulsive behavior, and engaging in pleasurable, high-risk behaviors. Symptoms of depression or a depressive episode include: an overly long period of sadness or hopelessness, loss of interest in activities, feeling tired, problems with concentration or memory, difficulty making decisions, being restless or irritable, change in eating or sleeping habits, and suicide ideation. Patients with bipolar disorder have a high risk of suicide and self-harm. The cause of bipolar disorder is not completely understood, but both genetic and environmental factors are thought to play a role. Environmental factors include long term stress and a history of child abuse.

Medications for treatment of the manic, psychotic, or depressive aspects of bipolar disorder generally include mood stabilizers, atypical antipsychotics, or antidepressants, in combination with psychotherapy. Sleep medications may also be used to help with sleep disturbances. For severe cases in which medication and psychotherapy does not work, electroconvulsive therapy may be used. Bipolar disorder usually is a lifelong illness and can worsen if left untreated. Long-term, continuous treatment is needed to control symptoms, and even with proper treatment mood changes can still occur. Patients frequently need to try several different medications before finding ones that help control symptoms. Given the unpleasant and potentially severe side effects associated with these medications, particularly anti-psychotic medications, a need exists to develop new therapeutics for treating mania in mood disorders and their related symptoms.

Schizophrenia affects approximately 1% of the adult population and reduces life expectancy by an average of 20 to 25 years through the impact of the disorder on self-care and physical health, as well as through suicide. At the present time the etiological mechanisms underlying schizophrenia are poorly understood. Schizophrenia is diagnosed clinically, based on characteristic symptoms of psychosis, disorganization and so called 'negative' symptoms (representing a reduced range of emotional expression, reduced production of speech and a lack of volition/motivation); duration of illness; impaired functioning; and the exclusion of other disorders such as autism and bipolar disorder. For clinicians, identifying which psychotic patients have schizophrenia requires clinical acumen and familiarity with the DSM-IV or ICD-10 diagnostic manuals [see, e.g., Corvin, *BMC Biol*. 2011; 9: 77].

Schizoaffective disorder is a mental health condition characterized primarily by symptoms of schizophrenia, such as hallucinations or delusions, and symptoms of a mood disorder, such as mania and depression. Diagnosis may be difficult as symptoms of schizophrenia and mood disorders are both present and many people are incorrectly diagnosed with schizophrenia or mood disorder. Treatment for schizoaffective disorder includes medications, typically antipsychotics and antidepressants and psychotherapy.

Antipsychotic drug therapy is a pillar in the treatment of schizophrenia. These antipsychotic drugs, also known as neuroleptics, generally cause a reduction of the 'positive' symptoms of schizophrenia, namely psychosis, thought disorders, and disorganized behavior. Antipsychotics generally have a lesser influence on cognition and on the 'negative' symptoms of the disease, which include lack of motivation and emotion, social withdrawal, lack of interest in everyday activities, and the reduced ability to plan or carry out activities.

Obsessive-compulsive disorder (OCD) is an anxiety disorder characterized by recurrent and persistent anxiety-provoking thoughts (obsessions) that lead to repetitive behaviors (compulsions) that focus on alleviating distress caused by obsessive thoughts. Patients may or may not recognize that the obsessions and compulsions are unreasonable, and these thoughts and behaviors can become time-consuming and impair function.

OCD is generally treated with psychotherapy, medication or both. Cognitive behavior therapy (CBT), which teaches a person different ways of thinking, behaving, and reacting to situations that help him or her to feel less anxious or fearful without having obsessive thoughts or acting compulsively (cognitive restructuring and exposure response prevention). However, CBT takes effort and practice to learn healthy ways to cope with anxiety. Medications may also be prescribed to treat OCD. The most commonly prescribed medications are anti-anxiety medications and anti-depressants. Anti-anxiety medications begin working right away, but should not be taken for long periods of time. Anti-depressants may take 10 to 12 weeks to start working and can cause side effects such as headache, nausea, sleep disturbance, and reduced libido. Atypical anti-psychotics may also be prescribed. It is not unusual for OCD patients to have to try several medications before finding one that controls OCD symptoms.

However, even when OCD is appropriately diagnosed and treated, many OCD patients are "treatment-resistant" or "treatment-refractory" and do not adequately respond to standard therapies. An estimated 10% to 40% of OCD patients are treatment-refractory (Bystritsky, Mol. Psychiatry 11:805-814). Treatment resistance generally refers to a lack of sufficient improvement despite multiple adequate and appropriate treatment trials. For mood disorders, it may be defined by failure to remit or respond clinically (50% reduction in symptoms) despite ≥2 adequate antidepressant trials or failure to respond clinically despite adequate medication trials across several neurotransmitter classes. Pallanti and Quercioli (Neuropsychopharmacol. Biol. Psychiatry 30:400-412) proposed categorizing obsessive-compulsive disorder treatment response into several stages along a spectrum, ranging from complete recovery (or remission) to full or partial response to non-response (or completely refractory). Whichever definition is used, patients with treatment resistance in anxiety disorders experience minimal restoration of function despite several appropriate treatment exposures. Factors that contribute to treatment resistance in OCD include, but are not limited to, disease severity, medical comorbidity, psychiatric comorbidity, treatment non-compliance, cultural factors, childhood stressors, long-term persistent stressors, life stage, and limitations of clinician/health system (Khalsa et al., Curr. Psychiatry, 2011, 10:45-52). Invasive therapies, including some that are irreversible, such as electroconvulsive therapy, vagal nerve stimulation, repetitive transcranial magnetic stimulation, and surgical methods, are reserved for patients with the strongest treatment resistance. More effective treatments are therefore needed to treat the symptoms associated with treatment refractory OCD.

Lesch-Nyhan syndrome is characterized by neurologic dysfunction, cognitive and behavioral disturbances, and uric acid overproduction and has a prevalence of 1:380,000. Patients with this syndrome suffer from cognitive deficits, movement disorders, and self-injurious behavior. The most common presenting feature of Lesch-Nyhan syndrome is developmental delay during the first year of life; hypotonia and delayed motor skills are usually evident by age 3-6 months. Children with Lesch-Nyhan syndrome typically fail to sit, crawl, and walk, and are ultimately confined to a wheelchair. Even with effective management of symptoms, most affected individuals survive only into their second or third decade.

Lesch-Nyhan syndrome is inherited in an X-linked recessive pattern and is caused by deficiency of the enzyme hypoxanthine-guanine phosphoribosyltransferase (HPRT) that catalyzes the conversion of hypoxanthine to inosine monophosphate (inosinic acid, IMP) and guanine to guanine monophosphate (guanylic acid, GMP) in the presence of phosphoribosyl pyrophosphate. To treat hyperuricemia and thereby reduce the risk for nephrolithiasis, urate nephropathy, gouty arthritis, and tophi, overproduction of uric acid is controlled with allopurinol, which blocks the metabolism of hypoxanthine and xanthine into uric acid catalyzed by xanthine oxidase.

Agitation in Alzheimer's disease refers to a cluster of several behavioral symptoms associated with the disease. Agitation develops as the disease progresses and occurs in addition to cognitive loss. The cluster of symptoms includes anxiety, depression, irritability, and motor restlessness (such as pacing, wandering, constant movement). Other symptoms that may occur include sleep disturbances, delusions, hallucinations, compulsive behaviors, aggression, and general emotional distress. Agitation may occur in as many as half of all individuals with Alzheimer's disease. Agitation is associated with patients who have a poor quality of life, deteriorating family relationships and professional caregivers, ultimately leading to admission to a residential care facility.

Fragile X syndrome (also called Martin-Bell syndrome) is a genetic condition that causes a range of developmental problems including learning disabilities and cognitive impairment. Usually, males are more severely affected by this disorder than females. Fragile X syndrome is inherited in an X-linked dominant pattern. Fragile X syndrome occurs in approximately 1 in 4,000 males and 1 in 8,000 females. This syndrome is caused by loss of the fragile X mental retardation protein (FMRP), generally due to transcriptional silencing from a CGG repeat expansion in the 5' untranslated region of the FMR1 gene (see, e.g., Verkerk et al., *Cell* 65:905-14 (1991)).

Affected individuals usually have delayed development of speech and language by the age of 2 years. Most males with Fragile X syndrome have mild to moderate intellectual disability, while about one-third of affected females are intellectually disabled. Children with Fragile X syndrome may also exhibit behavioral problems, including anxiety, attentional deficits, anxiety, and hyperactive behaviors, such as fidgeting or impulsive actions. Children with Fragile X syndrome and who have attentional deficits may be diagnosed with attention deficit disorder (ADD), which includes an impaired ability to maintain attention and difficulty focusing on specific tasks. About one-third of individuals with Fragile X syndrome have features of autism spectrum disorders that affect communication and social interaction, for example, anxiety and repetitive, stereotyped behaviors (i.e., stereotypies). Seizures occur in about 15 percent of males and about 5 percent of females with this syndrome.

The CGG repeat expansion in patients with Fragile X syndrome occurs more than 200 times. When the repeat expansion occurs to a lesser degree (i.e., between about 50-200 times), an FMR1 gene permutation occurs and FMRP is produced to some degree. FMR1 gene permutation may result in another genetic condition called Fragile X-associated tremor-ataxia syndrome (FXTAS). FXTAS is characterized by movement difficulties and cognition problems. FXTAS is a late-onset disorder, usually occurring after age 50; symptoms worsen with age. This condition also affects males more frequently and severely than females with about 1 in 3000 men affected.

Characteristics of FXTAS include problems with coordination and balance (ataxia) and intention tremor, which is trembling or shaking of a limb when the affected individual is trying to perform a voluntary movement, such as reaching for an object. Most often, intention tremors develop first, followed a few years later by ataxia. Not all persons with FXTAS have both features. Many affected individuals develop other movement problems, such as parkinsonism, which includes tremors when not moving (resting tremor), rigidity, and unusually slow movement (bradykinesia). In addition, affected individuals may have reduced sensation, numbness or tingling, pain, or muscle weakness in the lower limbs. Some people with FXTAS experience problems with the autonomic nervous system, leading to the inability to control the bladder or bowel.

Women who have a pre-mutation in their FMR1 gene are at higher risk for primary ovarian insufficiency (Fragile X-Associated Primary Ovarian Insufficiency) and are at higher risk for having children who have Fragile X syndrome. Fragile X-Associated Primary Ovarian Insufficiency is a cause of infertility and early menopause.

No uniformly effective intervention for managing the neurobehavioral aspects of Fragile X syndrome or FXTAS exists. More effective treatments are therefore needed to manage the conditions associated with these genetic diseases.

Autism spectrum disorder (ASD) is a range of complex neurodevelopment disorders, characterized by social impairments; communication difficulties; and restricted, repetitive, and stereotyped patterns of behavior (stereotypies). Autistic disorder, sometimes called autism or classical ASD, is the most severe form of ASD. Other conditions include a milder form known as Asperger syndrome, childhood disintegrative disorder, pervasive developmental disorder, which is not otherwise specified (usually referred to as PDD-NOS). Although ASD varies significantly in character and severity, it occurs in all ethnic and socioeconomic groups and affects every age group. Based on current data, experts estimate that about one of 70 children who are age eight will have an ASD. Males are four-five times more likely to have an ASD than females. The hallmark feature of ASD is impaired social interaction. Many children with an ASD engage in repetitive movements, such as rocking and twirling, or exhibit self-abusive behavior, such as biting or head-banging.

Depression is a common feature of mental illness, whatever its nature and origin. A person with a history of any serious psychiatric disorder has almost as high a chance of developing major depression as someone who has had major depression itself in the past. About 20% of the U.S. population reports at least one depressive symptom in a given month, and 12% report two or more in a year. Mood disorders represent a category of mental disorders in which the underlying problem primarily affects a person's persistent emotional state (their mood). Bipolar disorder is less common, occurring at a rate of 1% in the general population, but some believe the diagnosis is often overlooked because manic elation is too rarely reported as an illness. Bipolar disorder is an illness involving one or more episodes of serious mania and depression. Sometimes a person might only experience symptoms of mania. If a person only experiences feelings of sadness, this is considered depression. During episodes of bipolar disorder, a person's mood can swing from excessively "high" and/or irritable to sad and hopeless, with periods of a normal mood in between.

Major depressive disorder is one of the most common mental illnesses. Depression causes people to lose pleasure from daily life, can complicate other medical conditions, and can even be serious enough to lead to suicide. Depression can occur to anyone, at any age, and to people of any race or ethnic group. Depression is usually treated with medications, psychotherapy, or a combination of the two. Medications for major depressive disorder fall in multiple drug classes, including tricyclic antidepressants, monoamine oxidase inhibitors, selective serotonin reuptake inhibitors, and atypical antidepressants. However, most antidepressants require at least 4-6 weeks for onset of effectiveness, and many antidepressants have unpleasant side effects. Moreover, as many as two-thirds of patients with depression experience treatment failure with the first anti-depressant, and up to a third of patients with depression don't respond to several attempts at treatment. Given the unpleasant and potentially severe side effects associated with these medications, a need exists to develop new therapeutics for treating depression in mood disorders and their related symptoms.

Rett syndrome (RTT), originally termed cerebroatrophic hyperammonemia, is a rare genetic postnatal neurological disorder of the grey matter of the brain that affects both females and male patients, with predominance of female ones. Rett syndrome causes problems in brain function that are responsible for cognitive, sensory, emotional, motor, and autonomic function. Most frequent problems that occur include those involving learning, speech, sensory sensations, mood, movement, breathing, cardiac function, chewing, swallowing, and digestion. It is characterized by normal early growth and development followed by a slowing of development, loss of purposeful use of the hands, distinctive hand movements, slowed brain and head growth, problems with walking, seizures, and intellectual disability. In particular, repetitive stereotyped hand movements, such as wringing and/or repeatedly putting hands into the mouth, are usual symptoms. Apraxia—the inability to perform motor functions—is perhaps the most severely disabling feature of Rett syndrome, interfering with every body movement, including eye gaze and speech. Children with Rett syndrome often exhibit autistic-like behaviors in the early stages (http://www.ninds.nih.gov/disorders/rett/detail_rett.htm).

Nearly all cases of Rett syndrome are caused by a mutation in the methyl CpG binding protein 2, or MECP2 gene. The MECP2 gene contains instructions for the synthesis of a protein called methyl cytosine binding protein 2 (MeCP2), which is needed for brain development and acts as one of the many biochemical switches that can either increase gene expression or tell other genes when to turn off and stop producing their own unique proteins. Because the MECP2 gene does not function properly in individuals with Rett syndrome, insufficient amounts or structurally abnormal forms of the protein are produced and can cause other genes to be abnormally expressed. However, not everyone who has an MECP2 mutation has Rett syndrome. Although Rett syndrome is a genetic disorder, less than 1 percent of recorded cases are inherited or passed from one generation to the next. Most cases are spontaneous, which means the mutation occurs randomly. Rett syndrome is estimated to affect one in every 10,000 to 15,000 live female births and in all racial and ethnic groups worldwide.

Chorea-acanthocytosis (ChAc) is a neurological disorder that affects movements in many parts of the body. Chorea refers to the involuntary jerking movements made by people with this disorder. People with this condition also have abnormal star-shaped red blood cells (acanthocytosis). This disorder is one of a group of conditions called neuroacanthocytoses that involve neurological problems and abnormal red blood cells. Clinically is characterized by a Huntington disease-like phenotype with progressive neurological symptoms including movement disorders, psychiatric manifestations and cognitive disturbances. Chorea may also be associated with Huntington's disease, and the methods and compositions provided herein may be employed to treat the same.

Prevalence and incidence of chorea-acanthocytosis are not known, but it is estimated that there are around 1,000 cases worldwide. Onset is in early adulthood and the initial presentation is often subtle cognitive or psychiatric symptoms. During the course of the disease, most patients develop a characteristic phenotype including chorea. Most patients develop generalized chorea and some degree of parkinsonism. Impairment of memory and executive functions is frequent. Psychiatric manifestations are common and may present as schizophrenia-like psychosis or obsessive compulsive disorder (OCD). Chorea-acanthocytosis usually progresses slowly over 15-30 years, but sudden death, presumably caused by seizures or autonomic involvement, may occur.

Chorea-acanthocytosis is caused by various mutations in the VPS13A gene coding for chorein. No obvious genotype-phenotype correlations have been observed. This condition is inherited in an autosomal recessive pattern, which means both copies of the gene in each cell have mutations. The parents of an individual with an autosomal recessive condition each carry one copy of the mutated gene, but they typically do not show signs and symptoms of the condition.

As used herein, "22q11.2 Deletion Syndrome (22q11.2 DS) is also known as Velocardiofacial syndrome ("VCFS"), DiGeorge syndrome, CATCH 22 and less often referred to as DiGeorge sequence, Microdeletion 22q11.2, Monosomy 22q11, Conotruncal anomaly face syndrome, Sedlaĕlová syndrome, Shprintzen syndrome, Takao syndrome, or Cayler cardiofacial syndrome. It is an autosomal dominant genetic condition that arises from the deletion of genes on chromosome 22 at band q11.2. Approximately 90% of individuals with VCFS have a 3 Mb deletion with the deletion of two genes, COMT and TBX1, being specifically associated with VCFS. Only ~10% of individuals have a smaller 1.5 Mb deletion, which also typically includes the deletion of TBX1 and COMT. However, not all genes related to VCFS have been identified.

As used herein, "COMT" is a key enzyme for regulating catechol compounds, including dopamine, epinephrine and norepinephrine. Individuals with VCFS have approximately 50% less COMT mRNA, COMT protein expression, and enzyme activity compared to normal subjects. The characteristic behavioral manifestations of VCFS may be related to dopamine dysregulation resulting from COMT haploinsufficiency. However, that can be compounded by the presence of a low-activity COMT allele, leading to further dysregulation in patients with VCFS. COMT contains a common functional polymorphism, Val158Met (r54680), which leads to alterations in enzyme activity. Individuals with VCFS who have a single copy of the Met allele have markedly low COMT activity. Compared with VCFS adults carrying the COMT Val allele, those carrying the Met allele tend to have increased risk for psychotic disorders, other neuropsychiatric syndromes, and have more severe cognitive deficits.

Accordingly, in various embodiments as disclosed herein, methods are provided for treating a hyperkinetic movement disorder in a subject in need thereof by administering to the patient a therapeutically effective amount of the solid drug form of valbenazine or valbenazine ditosylate. In one embodiment, the hyperkinetic movement disorder is tardive dyskinesia, Tourette's syndrome, Huntington's disease, chorea associated with Huntington's disease, or tics. In other embodiments, the hyperkinetic movement disorder is ataxia, chorea, dystonia, hemifacial spasm, myoclonus, restless leg syndrome, or tremors.

In other embodiments, methods are provided for treating a neurological and/or psychiatric diseases and disorders in a subject in need thereof by administering to the patient a therapeutically effective amount of the solid drug form of valbenazine or valbenazine ditosylate. In one embodiment, the neurological and/or psychiatric disease or disorder is hyperkinetic movement disorder, mood disorder, bipolar disorder, schizophrenia, schizoaffective disorder, mania in mood disorder, depression in mood disorder, treatment-refractory obsessive compulsive disorder, neurological dysfunction associated with Lesch-Nyhan syndrome, agitation associated with Alzheimer's disease, Fragile X syndrome or Fragile X-associated tremor-ataxia syndrome, autism spectrum disorder, Rett syndrome, or chorea-acanthocytosis.

As used herein, "subject" means a mammal, including a human. The term "patient" is used synonymously with "subject" within this disclosure.

As used herein, the phrase term "therapeutically effective amount" refers to an amount of a therapeutic agent to treat, ameliorate, or prevent a disease or condition, or to exhibit a detectable therapeutic or preventative effect. The effect is detected by, for example, a reduction in tumor size. The effect is also detected by, for example, chemical markers, steroid levels, or antigen levels. Therapeutic effects also include reduction in physical symptoms, such as decreased body temperature. The precise effective amount for a subject will depend upon the subject's size and health, the nature and extent of the condition, the therapeutics or combination of therapeutics selected for administration, and other variables known to those of skill in the art. The effective amount for a given situation is determined by routine experimentation and is within the judgment of the clinician.

As used herein, "treatment" includes therapeutic applications to slow or stop progression of a disorder, prophylactic application to prevent development of a disorder, and/or reversal of a disorder. Reversal of a disorder differs from a therapeutic application which slows or stops a disorder in that with a method of reversing, not only is progression of a disorder completely stopped, cellular behavior is moved to some degree, toward a normal state that would be observed in the absence of the disorder.

As used herein, "capsule size" or "capsule size number" refers to the internationally accepted numbering system for capsule sizes used in approved U.S. drug products, as shown in Table 1 below.

TABLE 1

| Capsule Size | 000 | 00E | 00 | 0E | 0 | 1 | 2 | 3 | 4 | 5 |
|---|---|---|---|---|---|---|---|---|---|---|
| Empty Capsule Volume Capacity (ml) | | | | | | | | | | |
| Capacity | 1.37 | 1.00 | 0.90 | 0.78 | 0.68 | 0.48 | 0.36 | 0.27 | 0.20 | 0.13 |
| Empty Capsule Overall Closed Length | | | | | | | | | | |
| (mm) | 26.1 | 25.3 | 23.4 | 23.5 | 21.6 | 19.4 | 17.6 | 15.7 | 14.3 | 11.1 |
| Tolerance (mm) | ±0.3 | ±0.3 | ±0.3 | ±0.3 | ±0.3 | ±0.3 | ±0.3 | ±0.3 | ±0.3 | ±0.4 |

TABLE 1-continued

| Capsule Size | 000 | 00E | 00 | 0E | 0 | 1 | 2 | 3 | 4 | 5 |
|---|---|---|---|---|---|---|---|---|---|---|
| Empty Capsule Individual Lengths (Cap) | | | | | | | | | | |
| Cap (mm) | 12.95 | 12.95 | 11.80 | 11.68 | 10.85 | 9.85 | 8.80 | 8.00 | 7.20 | 6.20 |
| Tolerance | ±0.35 | ±0.35 | ±0.35 | ±0.35 | ±0.35 | ±0.35 | ±0.35 | ±0.35 | ±0.35 | ±0.29 |
| Empty Capsule Individual Lengths (Body) | | | | | | | | | | |
| Body (mm) | 22.20 | 22.20 | 20.22 | 20.19 | 18.35 | 16.40 | 15.15 | 13.45 | 12.10 | 9.30 |
| Tolerance | ±0.35 | ±0.35 | ±0.35 | ±0.35 | ±0.35 | ±0.35 | ±0.35 | ±0.35 | ±0.35 | ±0.29 |
| Empty Capsule External Diameter | | | | | | | | | | |
| Cap (mm) | 9.91 | 8.58 | 8.56 | 7.65 | 7.64 | 6.96 | 6.39 | 5.85 | 5.33 | 4.91 |
| Body (mm) | 9.55 | 8.25 | 8.23 | 7.36 | 7.35 | 6.63 | 6.12 | 5.6 | 5.08 | 4.68 |

As used herein, "blend uniformity" refers to the homogeneity of a solid and can represent either one sample or the average of more than one sample.

As used herein, "content uniformity" refers to the homogeneity of the valbenazine content among unit dosage forms, e.g. capsules, after formulation.

As used herein, "stratified sampling" refers to a process of selecting units deliberately from various locations within a lot or batch or from various phases or periods of a process to obtain a sample. In some embodiments, stratified sampling of the blend and dosage units specifically targets locations either in the blender or throughout the compression/filling operation, which have a higher risk of producing failing content uniformity results.

In various embodiments a solid pharmaceutical composition is provided of valbenazine, or a pharmaceutically acceptable salt thereof, silicified microcrystalline cellulose, isomalt, hydroxypropyl methylcellulose, partially pregelatinized maize starch, and magnesium stearate. In one embodiment, the pharmaceutically acceptable salt is valbenazine ditosylate.

In various embodiments, valbenazine, or a pharmaceutically acceptable salt thereof, is present in the solid pharmaceutical composition at a level ranging from about 20-160 mg as measured as the free base. In one embodiment, valbenazine, or a pharmaceutically acceptable salt thereof, is present at a level of about 20 mg as measured as the free base. In one embodiment, valbenazine, or a pharmaceutically acceptable salt thereof, is present at a level of about 40 mg as measured as the free base. In one embodiment, valbenazine, or a pharmaceutically acceptable salt thereof, is present at a level of about 60 mg as measured as the free base. In one embodiment, valbenazine, or a pharmaceutically acceptable salt thereof, is present at a level of about 80 mg as measured as the free base. In one embodiment, valbenazine, or a pharmaceutically acceptable salt thereof, is present at a level of about 100 mg as measured as the free base. In one embodiment, valbenazine, or a pharmaceutically acceptable salt thereof, is present at a level of about 120 mg as measured as the free base. In one embodiment, valbenazine, or a pharmaceutically acceptable salt thereof, is present at a level of about 140 mg as measured as the free base. In one embodiment, valbenazine, or a pharmaceutically acceptable salt thereof, is present at a level of about 160 mg as measured as the free base.

In one embodiment, valbenazine ditosylate is present in a unit dosage form of a solid pharmaceutical composition at a level of at least 30% by weight of the total weight of the unit dosage form. In one embodiment, valbenazine ditosylate is present at a level of at least 35% by weight of the total weight of the unit dosage form. In one embodiment, valbenazine ditosylate is present at a level of at least 38% by weight of the total weight of the unit dosage form. In one embodiment, valbenazine ditosylate is present at a level of at least 40% by weight of the total weight of the unit dosage form. In one embodiment, valbenazine ditosylate is present at a level of at least 45% by weight of the total weight of the unit dosage form.

In one embodiment, a solid pharmaceutical composition of valbenazine, or a pharmaceutically acceptable salt thereof, is provided where the solid pharmaceutical composition is in unit dosage form suitable for oral administration. In one embodiment, the unit dosage form is formulated for dosing once daily. In another embodiment, the unit dosage form is formulated for dosing twice, three times, or four times daily.

In one embodiment, a unit dosage form of a solid pharmaceutical composition of valbenazine, or a pharmaceutically acceptable salt thereof, as presented herein, is provided where the unit dosage form is in capsule form. In one embodiment, the unit dosage form is an oral dosage product. In one embodiment, the capsule is size 0 or smaller. In one embodiment, the capsule is size 1 or smaller. In one embodiment, the capsule is size 2 or smaller. In one embodiment, the capsule is size 3 or smaller.

In one embodiment, the unit dosage form capsule of the solid pharmaceutical composition of valbenazine, or a pharmaceutically acceptable salt thereof, as presented herein, has at least 80% dissolution at 30 minutes in a USP Paddle Dissolution Method 2 apparatus and 0.1 N HCl medium.

In another embodiment, the solid pharmaceutical composition of valbenazine or valbenazine ditosylate as presented herein has a bulk density of at least about 0.5 mg/mL. In another embodiment, the solid pharmaceutical composition of valbenazine or valbenazine ditosylate as presented herein has a tapped density of at least about 0.6 mg/mL. In another embodiment, valbenazine ditosylate in the solid pharmaceutical composition has a d(0.9) particle size distribution less than 100 μm.

In another embodiment, a unit dosage form of a pharmaceutical composition is provided having a capsule of size 1 or smaller and at least 80 mg of valbenazine, or a pharmaceutically acceptable salt thereof, as measured as the free base. In another embodiment, the valbenazine 80 mg unit dosage form has a capsule of size 2 or smaller. In another embodiment, the valbenazine 80 mg unit dosage form has a capsule of size 3 or smaller.

In another embodiment, a unit dosage form of a pharmaceutical composition is provided having a capsule of size 2 or smaller and at least 20 mg of valbenazine, or a pharmaceutically acceptable salt thereof, as measured as the free base. In another embodiment, the valbenazine 20 mg unit dosage form has a capsule of size 3 or smaller.

In another embodiment, a unit dosage form of a pharmaceutical composition is provided having a capsule of size 2 or smaller and at least 40 mg of valbenazine, or a pharmaceutically acceptable salt thereof, as measured as the free base. In another embodiment, the valbenazine 40 mg unit dosage form has a capsule of size 3 or smaller.

In one embodiment, a unit dosage form of a pharmaceutical composition is provided having a capsule of size 0 or smaller and at least 120 mg of valbenazine, or a pharmaceutically acceptable salt thereof, as measured as the free base. In another embodiment, the valbenazine 120 mg unit dosage form has a capsule of size 1 or smaller. In another embodiment, the valbenazine 80 mg unit dosage form has a capsule of size 2 or smaller.

In another embodiment, a unit dosage form of a pharmaceutical composition is provided with valbenazine ditosylate having a w/w % of at least 35%. In another embodiment, the valbenazine ditosylate has a w/w % of at least 38%. In another embodiment, the valbenazine ditosylate has a w/w % of at least 40%. In another embodiment, the unit dosage form further comprises silicified microcrystalline cellulose, isomalt, hydroxypropyl methylcellulose, partially pregelatinized maize starch, and magnesium stearate.

In one embodiment, a unit dosage form of a pharmaceutical composition is provided with valbenazine ditosylate having a w/w % of about 40%, silicified microcrystalline cellulose having a w/w % of about 25%, isomalt having a w/w % of about 20%, hydroxypropyl methylcellulose having a w/w % of about 5%, partially pregelatinized maize starch having a w/w % of about 7.5%, and magnesium stearate having a w/w % of about 2.5%.

Also provided is a unit dosage form comprising a solid composition described herein.

In some embodiments, the unit dosage form has an average stratified content uniformity of between about 99% and about 100% with a standard deviation of the mean of less than about 3.5%.

In some embodiments, the unit dosage form has an average stratified content uniformity of between about 99% and about 100% with a standard error of the mean of less than about 3.5%.

In one embodiment is provided a method of orally administering a unit dosage form valbenazine or valbenazine ditosylate to a subject in need thereof. In some embodiments, the subject has a neurological or psychiatric disease or disorder. In one embodiment, the subject has a hyperkinetic movement disorder. In another embodiment, the hyperkinetic movement disorder is tardive dyskinesia, Tourette's syndrome, Huntington's disease, or tics.

In some embodiments, the hyperkinetic movement disorder is tardive dyskinesia. In some embodiments, the hyperkinetic movement disorder is Tourette's syndrome. In some embodiments, the hyperkinetic movement disorder is Huntington's disease. In some embodiments, the hyperkinetic movement disorder is tics.

In some embodiments, the hyperkinetic movement disorder is chorea associated with Huntington's disease. In some embodiments, the hyperkinetic movement disorder is ataxia, chorea, dystonia, Huntington's disease, myoclonus, restless leg syndrome, or tremors.

In some embodiments, the patient has been determined to have 22q11.2 deletion syndrome. In some embodiments, the patient is predisposed to developing a psychiatric disorder due to the patient having 22q11.2 deletion syndrome. In some embodiments, the patient has been determined to have COMT haploinsufficiency. In some embodiments, the patient is predisposed to developing a psychiatric disorder due to the patient having COMT haploinsufficiency.

In some embodiments, the neurological or psychiatric disease or disorder is a hyperkinetic movement disorder, mood disorder, bipolar disorder, schizophrenia, schizoaffective disorder, mania in mood disorder, depression in mood disorder, treatment-refractory obsessive compulsive disorder, neurological dysfunction associated with Lesch-Nyhan syndrome, agitation associated with Alzheimer's disease, Fragile X syndrome or Fragile X-associated tremor-ataxia syndrome, autism spectrum disorder, Rett syndrome, or chorea-acanthocytosis.

In one embodiment is provided a method for treating a hyperkinetic movement disorder in a patient in need thereof by administering to the patient a therapeutically effective amount of the solid drug form of valbenazine or valbenazine ditosylate, as presented herein. In another embodiment, the hyperkinetic movement disorder is tardive dyskinesia, Tourette's syndrome, Huntington's disease, or tics.

Also provided is a unit dosage form, as described herein, for use in a method of treating a neurological or psychiatric disease or disorder of a patient in need thereof.

In the practice of the methods disclosed herein, valbenazine or pharmaceutically acceptable salt thereof may be administered to the patient for a first period of time followed by a second period of time, wherein valbenazine or pharmaceutically acceptable salt is administered at a lower level during the first period of time than the second period of time. The first period of time may be, for example, days, weeks or months. In one embodiment, the first period of time is one week. When administered daily in oral unit dosage form, valbenazine or pharmaceutically acceptable salt thereof may be present in a first unit dosage form at a level of about 40 mg as measured as the free base. Following a period of time, such as one week, a second daily oral unit dosage form may then be administered. For example, valbenazine or pharmaceutically acceptable salt thereof may be present in the second unit dosage form at a level of about 80 mg as measured as the free base.

In one embodiment, a kit is provided with a plurality of oral unit dosage forms of a solid pharmaceutical composition of valbenazine or valbenazine ditosylate in combination with instructions for administration.

In one embodiment, a kit is provided with a plurality of oral unit dosage forms of a solid composition of valbenazine or valbenazine ditosylate in combination with instructions for administration.

In one embodiment, a method for producing a unit dosage form of valbenazine ditosylate is provided according to FIG. 1.

Also provided is a process for preparing a solid composition of valbenazine, or a pharmaceutically acceptable salt thereof, wherein the process comprises:

a) subjecting a blend of valbenazine, or a pharmaceutically acceptable salt thereof, at least one water insoluble filler, and at least one water soluble diluent to comminution;

b) blending the product of step a) with at least one binder and at least one disintegrant;

c) determining the blend uniformity of the product of step b); and d) blending the product of step b) with at least one lubricant only if the blend uniformity satisfies a predetermined criteria to produce a solid pharmaceutical composition of valbenazine, or a pharmaceutically acceptable salt thereof.

In some embodiments, the process further comprises the steps of: e) determining density and/or particle size distribution of the product of step d); and f) subjecting the product of step d) to dry granulation to produce granules of valbenazine, or a pharmaceutically acceptable salt thereof, only if the density and/or particle size distribution satisfies a predetermined criteria.

In some embodiments, the process further comprises the steps of: g) determining density and/or particle size distribution of the product of step 0; and h) blending the granules of step f) with at least one lubricant only if the density and/or particle size distribution satisfies a predetermined criteria.

In some embodiments, the process further comprises the steps of: i) determining density and/or blend uniformity of the product of step h); and j) encapsulating the product of step h) to produce a unit dosage form comprising valbenazine, or a pharmaceutically acceptable salt thereof, only if the density and/or blend uniformity satisfies a predetermined criteria.

In some embodiments, the process further comprises the step of: determining the disintegration and/or content uniformity of the unit dosage form.

Methods for determining disintegration, content uniformity, density, particle size distribution, and blend uniformity are known in the art, including the methods described in U.S. Pharmacopeia ("USP") 905 (Uniformity of Dosage Units (2016)); USP 711 (Dissolution (2011)); USP 616 (Bulk Density and Tapped Density of Powders (2015)); USP 429 (Light Diffraction Measurement of Particle Size (2016)); and USP 701 (Disintegration (2016)), each of which is incorporated herein by reference for all purposes.

Also provided is a process for preparing a unit dosage form comprising valbenazine, or a pharmaceutically acceptable salt thereof, wherein the process comprises: encapsulating solid composition as described herein, to produce the unit dosage form comprising valbenazine, or a pharmaceutically acceptable salt thereof.

Also provided is a process for preparing a unit dosage form comprising valbenazine, or a pharmaceutically acceptable salt thereof, wherein the process comprises: encapsulating a lubricated blend to produce a solid composition comprising valbenazine, or a pharmaceutically acceptable salt thereof, wherein the lubricated blend comprises granules of valbenazine, or a pharmaceutically acceptable salt thereof, and at least one lubricant.

In some embodiments, the lubricated blend is prepared by a process comprising the steps of: blending at least one lubricant with granules of valbenazine, or a pharmaceutically acceptable salt thereof, to produce a lubricated blend.

In some embodiments, the granules of valbenazine, or a pharmaceutically acceptable salt thereof, is prepared by a process comprising the steps of: dry granulating a blend to produce granules of valbenazine, or a pharmaceutically acceptable salt thereof. In some embodiments, dry granulating a blend comprises gravity feeding the blend through the roller compactor.

In some embodiments, the blend is prepared by a process comprising the steps of: blending at least one lubricant with an intragranular blend to produce the blend.

In some embodiments, the intragranular blend is prepared by a process comprising blending a pre-blend with at least one disintegrant and at least one binder to produce the intragranular blend.

In some embodiments, the pre-blend is prepared by a process comprising the steps of: blending valbenazine, or a pharmaceutically acceptable salt thereof, with at least one water-insoluble filler and at least one water soluble diluent to produce the pre-blend.

Also provided is a process for preparing a unit dosage form comprising valbenazine, or a pharmaceutically acceptable salt thereof, wherein the process comprises:

preparing a dispersion of valbenazine, or a pharmaceutically acceptable salt thereof, in at least one water-insoluble filler and at least one water soluble diluent to produce a pre-blend;

blending the pre-blend with one or more excipients to produce a blend;

granulating the blend to produce a granulated blend;

optionally blending the granulated blend with one or more excipients to produce a lubricated blend; and encapsulating the lubricated blend.

Also provided is a unit dosage form comprising valbenazine, or a pharmaceutically acceptable salt thereof, prepared by any of the processes described herein.

Also provided is a solid composition of valbenazine, or a pharmaceutically acceptable salt thereof, and at least one pharmaceutically acceptable excipient, wherein the solid composition has a bulk density of at least about 0.5 mg/mL.

Also provided is a solid composition of valbenazine, or a pharmaceutically acceptable salt thereof, and at least one pharmaceutically acceptable excipient, wherein the solid composition has a tapped density of at least about 0.6 mg/mL.

Also provided is a solid composition of valbenazine, or a pharmaceutically acceptable salt thereof, and at least one pharmaceutically acceptable excipient, wherein the solid composition has a d(0.9) particle size distribution less than 100 μm.

Also provided is a solid composition of valbenazine, or a pharmaceutically acceptable salt thereof, and at least one pharmaceutically acceptable excipient, wherein the solid composition has a blend uniformity between about 90% and about 110% with a relative standard deviation of the blend uniformity of less than about 2%. In some embodiments, the solid composition has a blend uniformity between about 95% and about 105% with a relative standard deviation of the blend uniformity of less than about 2%.

Also provided is a solid composition of valbenazine, or a pharmaceutically acceptable salt thereof, and at least one pharmaceutically acceptable excipient, wherein the solid composition has a blend uniformity between about 90% and about 110% with a standard deviation of the blend uniformity of less than about 2%. In some embodiments, the solid composition has a blend uniformity between about 95% and about 105% with a standard deviation of the blend uniformity of less than about 2%.

In some embodiments, the valbenazine, or a pharmaceutically acceptable salt thereof, is present at a level ranging from about 20-160 mg as measured as the free base. In some embodiments, the valbenazine, or a pharmaceutically acceptable salt thereof, is present at a level of about 20 mg as measured as the free base. In some embodiments, the valbenazine, or a pharmaceutically acceptable salt thereof, is present at a level of about 40 mg as measured as the free base. In some embodiments, the valbenazine, or a pharmaceutically acceptable salt thereof, is present at a level of about 60 mg as measured as the free base. In some embodiments, the valbenazine, or a pharmaceutically acceptable salt thereof, is present at a level of about 80 mg as measured as the free base. In some embodiments, the valbenazine, or a pharmaceutically acceptable salt thereof, is present at a level of about 120 mg as measured as the free base. In some embodiments, the valbenazine, or a pharmaceutically acceptable salt thereof, is present at a level of about 160 mg as measured as the free base.

In some embodiments, the solid composition comprises valbenazine, or a pharmaceutically acceptable salt thereof, as measured by the free base, at a level of at least about 35% w/w. In some embodiments, the solid composition comprises valbenazine, or a pharmaceutically acceptable salt thereof, as measured by the free base, at a level of at least about 38% w/w. In some embodiments, the solid composition comprises valbenazine, or a pharmaceutically acceptable salt thereof, as measured by the free base, at a level of at least about 40% w/w. In some embodiments, the solid composition comprises valbenazine, or a pharmaceutically acceptable salt thereof, as measured by the free base, at a level of at least about 45% w/w. In some embodiments, the solid composition comprises valbenazine, or a pharmaceutically acceptable salt thereof, as measured by the free base, at a level of about 40% w/w.

In some embodiments, the pharmaceutically acceptable salt of valbenazine is a tosylate salt. In some embodiments, the pharmaceutically acceptable salt of valbenazine is valbenazine ditosylate.

In some embodiments, the solid composition comprises granules of the valbenazine, or a pharmaceutically acceptable salt thereof, and the at least one pharmaceutically acceptable excipient. In some embodiments, the granules are prepared by dry granulation. In some embodiments, the granules are prepared by roller compaction.

In some embodiments, the solid composition comprises a blend of the granules of valbenazine, or a pharmaceutically acceptable salt thereof, and the at least one pharmaceutically acceptable excipient with at least one lubricant.

In some embodiments, the at least one pharmaceutically acceptable excipient is at least one lubricant. In some embodiments, the solid composition comprises at least one lubricant in an amount of between about 0.25% and about 5% w/w. In some embodiments, the solid composition comprises at least one lubricant in an amount of about 2.5% w/w. In some embodiments, the at least one lubricant is chosen from magnesium stearate, calcium stearate, stearic acid, talc, starch, and fumed silica (silicon dioxide). In some embodiments, the at least one lubricant is magnesium stearate.

In some embodiments, the at least one pharmaceutically acceptable excipient is at least one disintegrant. In some embodiments, the at least one disintegrant is present in an amount of between about 1% and about 10% w/w, such as between about 2% and about 9%, such as between about 3% and about 8%, such as between about 4% and about 8%, such as between about 5% and about 8%, such as between about 6% and about 8%, such as between about 7% and about 8%. In some embodiments, the at least one disintegrant is present in an amount of about 7.5% w/w. In some embodiments, the at least one disintegrant is chosen from starch, alginic acid, sodium starch glycolate, croscarmellose, crospovidone, cellulose, and acid-carbonate effervescent systems. In some embodiments, the at least one disintegrant is starch.

In some embodiments, the at least one pharmaceutically acceptable excipient is at least one binder. In some embodiments, the at least binder is present in an amount of between about 0.5% and about 5% w/w, such as between about 2 and about 5%, such as between about 3% and about 5%, such as between about 4% and about 5%. In some embodiments, the at least binder is present in an amount of about 5% w/w. In some embodiments, the at least one binder is chosen from hypromellose, polyvinylpyrrolidone, natural gums (e.g. acacia gum), microcrystalline cellulose, methylcellulose, ethylcellulose, sucrose, starch, and gelatin. In some embodiments, the at least one binder is hypromellose.

In some embodiments, the at least one pharmaceutically acceptable excipient is at least one water soluble diluent. In some embodiments, the at least one water soluble diluent is present in an amount of between about 20% and about 95% w/w, such as between about 20% and about 80%, such as between about 20% and about 60%, such as between about 20% and about 40%. In some embodiments, the at least one water soluble diluent is present in an amount of about 20% w/w. In some embodiments, the at least one water soluble diluent is chosen from lactose, mannitol, isomalt, sucrose, dextrose, and sorbitol. In some embodiments, the at least one water soluble diluent is isomalt.

In some embodiments, the at least one pharmaceutically acceptable excipient is at least one water insoluble filler. In some embodiments, the at least one insoluble filler is present in an amount of between about 20% and about 95% w/w, such as between about 20% and about 80%, such as between about 20% and about 60%, such as been about 20% and about 40%. In some embodiments, the at least one insoluble filler is present in an amount of about 25% w/w. In some embodiments, the at least one water soluble filler is chosen from microcrystalline cellulose, starch, dicalcium phosphate dihydrate, and calcium carbonate. In some embodiments, the at least one water soluble filler is microcrystalline cellulose.

In some embodiments, the solid composition is a solid pharmaceutical composition.

Also provided is an oral dosage product comprising the solid composition described herein.

Also provided is a unit dosage form prepared from a solid composition of valbenazine, or a pharmaceutically acceptable salt thereof, and at least one pharmaceutically acceptable excipient, wherein the solid composition has a bulk density of at least about 0.5 mg/mL.

Also provided is a unit dosage form prepared from a solid composition of valbenazine, or a pharmaceutically acceptable salt thereof, and at least one pharmaceutically acceptable excipient, wherein the solid composition has a tapped density of at least about 0.6 mg/mL.

Also provided is a unit dosage form prepared from a solid composition of valbenazine, or a pharmaceutically acceptable salt thereof, and at least one pharmaceutically acceptable excipient, wherein the solid composition has a d(0.9) particle size distribution less than 100 µm.

Also provided is a unit dosage form prepared from a solid composition of valbenazine, or a pharmaceutically acceptable salt thereof, and at least one pharmaceutically acceptable excipient, wherein the solid composition has a blend uniformity between about 90% and about 110% with a relative standard deviation of the blend uniformity of less than about 2%.

Also provided is a unit dosage form prepared from a solid composition of valbenazine, or a pharmaceutically acceptable salt thereof, and at least one pharmaceutically acceptable excipient, wherein the solid composition has a blend uniformity between about 90% and about 110% with a standard deviation of the blend uniformity of less than about 2%.

In one embodiment, a composition is provided of valbenazine, or a pharmaceutically acceptable salt thereof, silicified microcrystalline cellulose, isomalt, hydroxypropyl methylcellulose, partially pregelatinized maize starch, and magnesium stearate. In another embodiment, the composition has appropriate properties for unit dosage manufacture, including de-agglomeration, granule flow, blending, uniformity, compression, encapsulation characteristics, dry granulation parameters and granule characteristics.

Physical characteristics of the granules and a final lubricated blend include bulk and tapped densities, flowdex, and particle size distribution (PSD). In one embodiment, the composition has blend uniformity for final lubricated blends, encapsulation fill weight uniformity and dissolution profiles and content uniformity. Content and uniformity of dosage units is prepared by adequate de-agglomeration and subsequent dispersion of the drug substance in isomalt and silicified microcrystalline cellulose diluents. Improper processing parameters can result in poor granule flow and compressibility which can impact encapsulation.

Blending is performed in a controlled environment minimizing moisture exposure. Inadequate blending can impact content and uniformity of dosage units. Over blending with hydrophobic magnesium stearate can impact dissolution.

Each and every process, method, composition, or use described herein optionally includes the limitation "wherein the oral dosage form is not a capsule comprising 80 mg valbenazine free base in combination with hypromellose, isomalt, magnesium stearate, pregelatinized starch, and silicified microcrystalline cellulose."

Each and every process, method, composition, or use described herein optionally includes the limitation "wherein the oral dosage form is not a capsule comprising 40 mg valbenazine free base in combination with colloidal silicon dioxide, magnesium stearate, mannitol, and pregelatinized starch."

Each and every process, method, composition, or use described herein optionally includes the limitation "wherein the oral dosage form is not a capsule comprising 80 mg valbenazine free base in combination with mannitol, partially pregelatinized maize starch, fumed silica, and magnesium stearate."

Each and every process, method, composition, or use described herein optionally includes the limitation "wherein the oral dosage form is not a capsule comprising 40 mg valbenazine free base in combination with mannitol, partially pregelatinized maize starch, fumed silica, and magnesium stearate."

EXAMPLES

Example 1

Preparation of Capsule Containing 80 Mg Valbenazine

Capsules containing 80 mg valbenazine (measured as the free base) may be prepared according to the procedure set forth below, and the makeup of exemplary tablets are listed in Table 2. A flow diagram of the manufacturing process for Valbenazine Capsules, 80 mg, which comprises unit operations of low shear (tumble) blending, screening, roller compaction and encapsulation, is presented in FIG. 1.

TABLE 2

| Component | Quantity 80 mg capsule | | |
|---|---|---|---|
| | (mg/capsule) | % (w/w) | Function |
| Valbenazine ditosylate | 145.80 | 40.0 | Active |
| Silicified Microcrystalline Cellulose | 91.25 | 25.0 | Diluent |
| Isomalt | 73.00 | 20.0 | Diluent |
| Partially pregelatinized maize starch | 27.38 | 7.5 | Disintegrant |
| Hydroxypropyl Methylcellulose | 18.25 | 5.0 | Binder |
| Magnesium stearate | 9.12 | 2.5 | Lubricant |
| Total Capsule Fill Weight | 364.80 | 100.00 | — |
| Hard gelatin capsule - Size #1 | 1 | — | Shell |

Valbenazine ditosylate, silicified microcrystalline cellulose (USP), isomalt (United States National Formulary, "USNF"), partially pregelatinized maize starch (USNF), hydroxypropyl methylcellulose (USNF) and magnesium stearate (USNF) were weighed according to the amounts in Table 2.

Wallpapering:
Isomalt was transferred through a screening mill equipped with an 813 μm or equivalent round-hole screen to a tote bin for blending. The screened isomalt component was then blended.

Pre-Blending and Screening:
The following components were transferred into the tote bin through a screening mill equipped with a ~813 μm or equivalent round-hole screen:
a. Valbenazine ditosylate b. Silicified microcrystalline cellulose ("SMCC") The components were then blended.

Delumping:
The blend was vacuum transferred through a buffer tank equipped with a ~813 μm or equivalent round-hole screen.

Pre-Blending #2:
The screened components were again blended.

Intragranular Blending:
The following components were then transferred, into the tote bin through a screening mill equipped with a ~813 μm or equivalent round-hole screen:
a. Partially pregelatinized maize starch
b. Hydroxypropyl methylcellulose The components were then blended. Inadequate de-agglomeration and subsequent dispersion of valbenazine ditosylate in isomalt and SMCC diluent can potentially impact content and uniformity of dosage units.

Lubricant Blending:
Magnesium stearate was manually screened (~1 mm sieve) (intragranular quantity adjusted as needed based on pre-lubricated blend yield—limit 98%) into the opened tote bin for blending. The components were then blended. The desired output for this step is improved flowability with increased bulk and tapped density and improved particle size distribution.

Roller Compaction:
The blend was then gravity fed through a roller compactor with a mill screen of 0.8-1.0 mm. The blend characterisics are important factors to consider for how well the blend will handle during encapsulation. Improper processing parameters can result in poor granule flow and compressibility which impacts encapsulation. The high solubility of the API and excipients should not impact dissolution. All roller compaction blends showed improvement over the initial intragranular blend properties which supports better capsule weight uniformity.

Final Lubricant Blending:

Magnesium stearate was manually screened (∫1 mm sieve) (quantity to be adjusted as needed based on pre-lubricated blend yield—limit 98%) into the opened tote bin for blending. The components were then blended. The desired output for this step is a uniform and free flowing lubricated final blend for encapsulation. Inadequate blending can impact content and uniformity of dosage units. Over blending with hydrophobic magnesium stearate can impact dissolution. Blending is performed in a controlled environment minimizing moisture exposure.

Encapsulation:

The lubricated blend was transferred to an automatic encapsulation machine and encapsulated into a size 1 capsule. Improper encapsulation equipment setup can impact filled capsule shell appearance. Capsule fill weight can impact content and dose uniformity. Capsule fill plug compression could impact dissolution and fill weight/content uniformity.

Encapsulation is performed in a controlled environment minimizing moisture exposure.

Dedusting and metal detection of the encapsulated product was performed, and the product was weight-checked.

Example 2

Preparation of 80 Mg Valbenazine Capsule with Prior Art Formulation

An 80 mg dose formulation strategy attempted to use the known 40 mg capsule direct encapsulation formulation. Efforts were made to fill a Size 0 capsule with twice the amount of the 40 mg powder blend to yield an 80 mg strength capsule, as shown in Table 3.

TABLE 3

| | Quantity 80 mg capsule | | |
|---|---|---|---|
| Component | (mg/capsule) | % (w/w) | Function |
| Valbenazine ditosylate | 146.0 | 28.21 | Active |
| Mannitol | 320.0 | 61.82 | Diluent |
| Partially pregelatinized maize starch | 40.0 | 7.73 | Disintegrant |
| Fumed silica | 6.4 | 1.24 | Glidant |
| Magnesium stearate | 2.4 | 1.00 | Lubricant |
| Total Capsule Fill Weight | 517.6 | 100.00 | — |
| Hard gelatin capsule - Size #0 | 1 | — | Shell |

Valbenazine ditosylate, mannitol (USP), partially pregelatinized maize starch (USNF), fumed silica (USNF) and magnesium stearate (USNF) were weighed according to the amounts in Table 3. A portion of the mannitol (¼) was transferred through a screening mill equipped with a ~0.8 mm or equivalent round-hole screen to a tote bin for blending. The screened mannitol component was then blended.

Pre-Blending and Screening:

The following components were transferred into the tote bin through a screening mill equipped with a ~0.8 mm or equivalent round-hole screen:
  a. Valbenazine ditosylate
  b. Fumed silica
  c. Partially pregelatinized maize starch
  d. Remaining mannitol (¾)—(the adjustment of mannitol weight to compensate DS assay is performed on this fraction)

The components were blended and then transferred into polyethylene (PE) bags. The pre-blend was transferred through a screening mill equipped with an ~0.8 mm or equivalent round-hole screen to a tote bin for blending.

Final Lubricant Blending:

Magnesium stearate (quantity to be adjusted as needed based on pre-lubricated blend yield—limit 98%) was manually screened (~1 mm sieve) into the opened tote bin for blending. The components were then blended.

Encapsulation:

Efforts to fill a Size 0 capsule were unsuccessful. It was not possible to compress enough powder into a compact that would fit into a Size 0 capsule shell.

The various embodiments described above can be combined to provide further embodiments. This application also claims the benefit of U.S. Provisional Patent Application No. 62/561,629, filed Sep. 21, 2017 and U.S. Provisional Patent Application No. 62/564,951, filed Sep. 28, 2017, and are incorporated herein by reference in their entirety. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A solid pharmaceutical composition comprising:
   a ditosylate salt of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester;
   at least one water-insoluble filler;
   at least one water-soluble diluent;
   at least one binder;
   at least one disintegrant; and
   at least one lubricant,
   wherein the ditosylate salt is present in the solid pharmaceutical composition at a level of at least 30% by weight of the solid pharmaceutical composition.

2. The solid pharmaceutical composition of claim 1, wherein the ditosylate salt is present in the solid pharmaceutical composition at a level of at least 35% by weight of the solid pharmaceutical composition.

3. The solid pharmaceutical composition of claim 1, wherein the ditosylate salt is present in the solid pharmaceutical composition at a level of at least 38% by weight of the solid pharmaceutical composition.

4. The solid pharmaceutical composition of claim 1, wherein the ditosylate salt is present in the solid pharmaceutical composition at a level of at least 40% by weight of the solid pharmaceutical composition.

5. The solid pharmaceutical composition of claim 1, wherein said dosage form comprises:
   between 20% w/w and 40% w/w of the at least one water-insoluble filler;
   between 20% w/w and 40% w/w of the at least one water-soluble diluent;

between 0.5% w/w and 5% w/w of the at least one binder;
between 1% w/w and 10% w/w of the at least one disintegrant; and
between 0.25% w/w and 5% w/w of the at least one lubricant.

6. The solid pharmaceutical composition of claim 5, wherein the at least one water-insoluble filler is microcrystalline cellulose.

7. The solid pharmaceutical composition of claim 5, wherein the at least one water-soluble diluent is isomalt.

8. The solid pharmaceutical composition of claim 5, wherein the binder is hypromellose.

9. The solid pharmaceutical composition of claim 5, wherein the at least one disintegrant is partially pregelatinized maize starch.

10. The solid pharmaceutical composition of claim 5, wherein the at least one lubricant is magnesium stearate.

11. The solid pharmaceutical composition of claim 5, wherein the at least one water-insoluble filler is microcrystalline cellulose and is present in an amount of about 25% w/w.

12. The solid pharmaceutical composition of claim 5, wherein the at least one water-soluble diluent is isomalt and is present in an amount of about 20% w/w.

13. The solid pharmaceutical composition of claim 5, wherein the at least one binder is hypromellose and is present in an amount of about 5% w/w.

14. The solid pharmaceutical composition of claim 5, wherein the at least one disintegrant is partially pregelatinized maize starch and is present in an amount of about 7.5% w/w.

15. The solid pharmaceutical composition of claim 5, wherein the at least one lubricant is magnesium stearate and is present in an amount of about 2.5% w/w.

16. The solid pharmaceutical composition of claim 1, wherein the solid pharmaceutical composition is suitable for oral administration.

17. The solid pharmaceutical composition of claim 1, wherein the solid pharmaceutical composition has a bulk density of at least about 0.5 mg/mL.

18. The solid pharmaceutical composition of claim 1, wherein the solid pharmaceutical composition has a tapped density of at least about 0.6 mg/mL.

19. The solid pharmaceutical composition of claim 1, wherein the solid pharmaceutical composition has a blend uniformity between about 90% and about 110% with a relative standard deviation of the blend uniformity of less than about 2%.

20. The solid pharmaceutical composition of claim 1, wherein the ditosylate salt has a d(0.9) particle size distribution less than 100 µm.

21. The solid pharmaceutical composition of claim 1, wherein:
the ditosylate salt is present in the solid pharmaceutical composition at a level of at least 38% by weight of the solid pharmaceutical composition;
the at least one water-insoluble filler is microcrystalline cellulose and is present in an amount of about 25% w/w;
the at least one water-soluble diluent is isomalt and is present in an amount of about 20% w/w;
the at least one binder is hypromellose and is present in an amount of about 5% w/w;
the at least one disintegrant is partially pregelatinized maize starch and is present in an amount of about 7.5% w/w; and
the at least one lubricant is magnesium stearate and is present in an amount of about 2.5% w/w.

22. A method of treating a hyperkinetic movement disorder in a patient in need thereof, comprising orally administering to the patient the solid pharmaceutical composition of claim 1.

23. The method according to claim 22, wherein the hyperkinetic movement disorder is tardive dyskinesia.

24. The method according to claim 22, wherein the hyperkinetic movement disorder is chorea.

25. The method according to claim 24, wherein chorea is associated with Huntington's disease.

26. A method of treating a hyperkinetic movement disorder in a patient in need thereof, comprising orally administering to the patient the solid pharmaceutical composition of claim 21.

27. The method according to claim 26, wherein the hyperkinetic movement disorder is tardive dyskinesia.

28. The method according to claim 26, wherein the hyperkinetic movement disorder is chorea.

29. The method according to claim 28, wherein chorea is associated with Huntington's disease.

30. The solid pharmaceutical composition of claim 1, wherein the solid pharmaceutical composition comprises granules, wherein the granules comprise the ditosylate salt.

31. The solid pharmaceutical composition of claim 5, wherein the solid pharmaceutical composition comprises granules, wherein the granules comprise the ditosylate salt.

32. The solid pharmaceutical composition of claim 21, wherein the solid pharmaceutical composition comprises granules, wherein the granules comprise the ditosylate salt.

* * * * *